US008877202B2

(12) United States Patent
Govindan et al.

(10) Patent No.: US 8,877,202 B2
(45) Date of Patent: Nov. 4, 2014

(54) PRO-DRUG FORM (P2PDOX) OF THE HIGHLY POTENT 2-PYRROLINODOXORUBICIN CONJUGATED TO ANTIBODIES FOR TARGETED THERAPY OF CANCER

(71) Applicant: Immunomedics, Inc., Morris Plains, NJ (US)

(72) Inventors: Serengulam V. Govindan, Summit, NJ (US); William J. McBride, Boonton, NJ (US); Nalini Sathyanarayan, Edison, NJ (US); Christine Mazza-Ferreira, Park Ridge, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 14/175,089

(22) Filed: Feb. 7, 2014

(65) Prior Publication Data
US 2014/0219956 A1 Aug. 7, 2014

Related U.S. Application Data

(60) Provisional application No. 61/761,845, filed on Feb. 7, 2013, provisional application No. 61/810,002, filed on Apr. 9, 2013.

(51) Int. Cl.
*A61K 39/00* (2006.01)
*A61K 39/395* (2006.01)
*A61K 31/704* (2006.01)
*C07K 16/18* (2006.01)

(52) U.S. Cl.
CPC ............... *C07K 16/18* (2013.01); *A61K 31/704* (2013.01)
USPC ................... 424/181.1; 424/141.1; 424/178.1

(58) Field of Classification Search
CPC ........... A61K 39/395; A61K 47/48561; A61K 39/39558; A61K 2039/505; A61K 2300/00; A61K 47/48407; A61K 47/48569; A61K 47/48246; A61K 39/3955; A61K 51/1045
See application file for complete search history.

(56) References Cited

U.S. PATENT DOCUMENTS

| | | | |
|---|---|---|---|
| 4,816,567 A | 3/1989 | Cabilly et al. | |
| 5,196,522 A | 3/1993 | Farquhar et al. | |
| 5,521,290 A | 5/1996 | Sivam et al. | |
| 5,530,101 A | 6/1996 | Queen et al. | |
| 5,618,920 A | 4/1997 | Robinson et al. | |
| 5,693,762 A | 12/1997 | Queen et al. | |
| 5,708,146 A | 1/1998 | Willner et al. | |
| 5,736,137 A | 4/1998 | Anderson et al. | |
| 5,846,534 A | 12/1998 | Waldmann et al. | |
| 6,051,230 A | 4/2000 | Thorpe et al. | |
| 6,433,150 B2 | 8/2002 | Farquhar et al. | |
| 6,653,104 B2 | 11/2003 | Goldenberg et al. | |
| 7,151,164 B2 | 12/2006 | Hansen et al. | |
| 7,312,318 B2 | 12/2007 | Hansen et al. | |
| 7,534,427 B2 | 5/2009 | Goldenberg et al. | |
| 7,772,373 B2 | 8/2010 | Hansen et al. | |
| 7,829,064 B2 | 11/2010 | Griffiths et al. | |
| 7,919,087 B2 | 4/2011 | Hansen et al. | |
| 8,039,273 B2 * | 10/2011 | Jeffrey ......................... | 436/532 |
| 8,361,464 B2 | 1/2013 | Griffiths et al. | |
| 8,568,729 B2 | 10/2013 | Griffiths et al. | |
| 2002/0018749 A1 | 2/2002 | Hudson et al. | |
| 2004/0115193 A1 | 6/2004 | Hansen et al. | |
| 2005/0271671 A1 | 12/2005 | Griffiths et al. | |
| 2009/0068095 A1 | 3/2009 | Marasco et al. | |
| 2009/0326178 A1 | 12/2009 | Okamoto et al. | |
| 2011/0190291 A1 | 8/2011 | Renslo et al. | |
| 2012/0121613 A1 | 5/2012 | Tang et al. | |
| 2012/0321553 A1 | 12/2012 | Zeng et al. | |

FOREIGN PATENT DOCUMENTS

| | | |
|---|---|---|
| CN | 101503732 | 8/2009 |
| EP | 0476408 | 3/1992 |
| EP | 0495265 | 7/1992 |
| EP | 0624377 | 11/1994 |
| EP | 0665020 | 8/1995 |
| WO | 97/23243 | 7/1997 |
| WO | 98/50435 | 11/1998 |
| WO | 00/67795 | 11/2000 |
| WO | 00/74718 | 12/2000 |
| WO | 03034995 | 5/2003 |
| WO | 03/074566 | 9/2003 |
| WO | 03/074567 | 9/2003 |
| WO | 2004067038 | 8/2004 |

OTHER PUBLICATIONS

Alinari et al., "Combination anti-CD74 (milatuzumab) and anti-CD20 (rituximab) monoclonal antibody therapy has in vitro and in vivo activity in mantle cell lymphoma", Blood. Apr. 28, 2011;117(17):4530-41.

Beckman et al., "Antibody constructs in cancer therapy: protein engineering strategies to improve exposure in solid tumors", Cancer. Jan. 15, 2007;109(2):170-9.

Bendig, M., "Humanization of Rodent Monoclonal Antibodies by CDR Grafting", Academic Press Inc., New York, NY, vol. 8, (1995), pp. 83-93.

Berkova et al., "Milatuzumab—a promising new immunotherapeutic agent", Expert Opin Investig Drugs. Jan. 2010;19 (1):141-9.

(Continued)

*Primary Examiner* — Daniel C Gamett
(74) *Attorney, Agent, or Firm* — Richard A. Nakashima

(57) ABSTRACT

Disclosed are methods, compositions and uses of conjugates of prodrug forms of 2-pyrrolinodoxorubicin (P2PDox) with antibodies or antigen-binding fragments thereof (ADCs), with targetable construct peptides or with other targeting molecules that are capable of delivering the P2PDox to a targeted cell, tissue or pathogen. Once delivered to the target cell, the ADC or peptide conjugate is internalized, a highly toxic 2-pyrrolinodoxorubicin (2-PDox) is released intracellularly. The P2PDox-peptide or ADC conjugates are of use to treat a wide variety of diseases, such as cancer, autoimmune disease or infectious disease.

45 Claims, 22 Drawing Sheets

(56) References Cited

OTHER PUBLICATIONS

Brambilla et al., "Phase II study of doxorubicin versus epirubicin in advanced breast cancer", Cancer Treat Rep. Feb. 1986;70(2):261-6.
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Cespedes et al., "Mouse models in oncogenesis and cancer therapy", Clin Transl Oncol. May 2006;8(5):318-29.
Colman, P., "Effects of amino acid sequence changes on antibody-antigen interactions", Res. Immunol. 1994, 145:33-36.
Dennis et al., "Cancer: off by a whisker", Nature. Aug. 17, 2006;442(7104):739-41.
Di Stefano et al., "A novel method for coupling doxorubicin to lactosaminated human albumin by an acid sensitive hydrazone bond: synthesis, characterization and preliminary biological properties of the conjugate", Eur. J. Pharm. Sci. 23:393-397 (2004).
Froesch et al., "Preparation and functional evaluation of new doxorubicin immunoconjugates containing an acid-sensitive linker on small-cell lung cancer cells", Cancer Immunol Immunother. Jan. 1996;42(1):55-63.
Fujimori et al., "A modeling analysis of monoclonal antibody percolation through tumors: a binding-site barrier", J Nucl Med. Jul. 1990;31(7):1191-8.
Gold et al., "Enhanced expression of CD74 in gastrointestinal cancers and benign tissues", Int J Clin Exp Pathol. Nov. 23, 2010;4(1):1-12.
Gondo et al., "HLA class II antigen associated invariant chain gene expression in malignant lymphoma", Br. J. Haematol. Dec. 1987;67(4):413-7.
Griffiths et al., "Cure of SCID mice bearing human B-lymphoma xenografts by an anti-CD74 antibody-anthracycline drug conjugate", Clin Cancer Res. Dec. 15, 2003;9(17):6567-71.
Griffiths et al., "Promising Therapeutic Activity of a New Drug Immunoconjugate, IMMU-110, in a Human Burkitt Lymphoma Model", Blood Nov. 16, 2003;102(11):645A, Abstract # 2381.
Hansen et al., "Internalization and catabolism of radiolabelled antibodies to the MHC class-II invariant chain by B-cell lymphomas", Biochem. J. 1996, 320:293-300.
Human Protein Reference Database datasheet for CD74; pp. 1-2; Oct. 12, 2011.
Ibragimova et al., "Stability of the beta-sheet of the WW domain: A molecular dynamics simulation study", Biophys. J. Oct. 1999;77(4):2191-8.
Kaneko et al., "New hydrazone derivatives of adriamycin and their immunoconjugates—A correlation between acid stability and cytotoxicity", Bioconjug Chem. May-Jun. 1991;2(3):133-41.
King et al., "BR96 conjugates of highly potent anthracyclines", Bioorg Med Chem Lett. Jul. 7, 2003;13(13):2119-22.
King et al., "Monoclonal antibody conjugates of doxorubicin prepared with branched linkers: A novel method for increasing the potency of doxorubicin immunoconjugates", Bioconjug Chem. Mar.-Apr. 1999;10(2):279-88.
Kolata, G., "Clinical promise with new hormones", Science 236:517-519 (1987).
Lambert, J., "Drug-conjugated monoclonal antibodies for the treatment of cancer", Curr Opin Pharmacol. Oct. 2005;5 (5):543-9.
Lau et al., "Novel doxorubicin-monoclonal anti-carcinoembryonic antigen antibody immunoconjugate activity in vitro", Bioorg Med Chem. Oct. 1995;3(10):1305-12.
Lazar et al., "Transforming growth factor alpha: an aromatic side chain at position 38 is essential for biological activity", Mol. Cell. Biol. 8(3):1247-1252 (1988).
Michel et al., "Therapy of small subcutaneous B-lymphoma xenografts with antibodies conjugated to radionuclides emitting low-energy electrons", Clin Cancer Res. Jan. 15, 2005;11(2 Pt 1):777-86.
Moller et al., "CD74", J. Biol. Regul. Homeost. Agents Oct.-Dec. 2000;14(4):299-301.
Moore et al., "Antibody cross-competition analysis of the human immunodeficiency virus type 1 gp120 exterior envelope glycoprotein", J Virol. Mar. 1996;70(3):1863-72.
Mueller et al., "Antibody conjugates with morpholinodoxorubicin and acid-cleavable linkers", Bioconjug Chem. Sep.-Oct. 1990;1(5):325-30.
Nagy et al., "High yield conversion of doxorubicin to 2-pyrrolinodoxorubicin, an analog 500-1000 times more potent: structure-activity relationship of daunosamine-modified derivatives of doxorubicin", Proc Natl Acad Sci U S A. Mar. 19, 1996;93(6):2464-9.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Oster et al., "Erythropoietin for the Treatment of Anemia of Malignancy Associated with Neoplastic Bone Marrow Infiltration", J. Clin. Oncol., 8(6):956-962 (1990).
Perez-Soler et al., "Use of Drug Carriers to Ameliorate the Therapeutic Index of Anthracycline Antibodies", ACS Symposium Series; ACS; Washington, CD, 1994; 574:300-319.
Qu et al., "Internalization and Cytotoxic Effects of a Humanized Anti-CD74 Antibody, LL1", Proc. Am. Assoc. Cancer Res 2002;43:255.
Rudikoff et al., "Single amino acid substitution altering antigen-binding specificity", Proc. Natl. Acad. Sci. USA 1982; 79(6):1979-83.
Rudnick et al., "Affinity and avidity in antibody-based tumor targeting", Cancer Biother Radiopharm. Apr. 2009;24 (2):155-61.
Sapra et al., "Anti-CD74 Antibody-Doxorubicin Conjugate, IMMU-110, in a Human Multiple Myeloma Xenograft and in Monkeys" Clin Cancer Res. Jul. 15, 2005;11(14):5257-64.
Scott et al., "Synthesis of reagents for the one step incorporation of hydrazide functionality onto the lysine residues of proteins, and their use as linkers for carbonyl containing molecules", Bioorg Med Chem Lett. 6(13):1491-1496 (1996).
Shi et al., "Monoclonal antibody classification based on epitope-binding using differential antigen disruption", J Immunol Methods. Jul. 31, 2006;314(1-2):9-20.
Shih et al. "Localization of an antibody to CD74 (MHC class II invariant chain) to human B cell lymphoma xenografts in nude mice", Cancer Immunol. Immunother. 49:208-216 (2000).
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.
Trail et al., "Cure of Xenografted Human Carcinoma by BR96-Doxorubicin Immunoconjugates", Science Jul. 9, 1993;261(5118):212-5.
Tutt et al., "Monoclonal Antibody Therapy of B Cell Lymphoma: Signaling Activity on Tumor Cells Appears More Important Than Recruitment of Effectors", J. Immunol. 161(6):3176-85 (1998).
Van Der Geld et al., "Characterization of monoclonal antibodies to proteinase 3 (PR3) as candidate tools for epitope mapping of human anti-PR3 autoantibodies", Clin Exp Immunol. Dec. 1999;118(3):487-96.
Voskoglou-Nomikos et al., "Clinical predictive value of the in vitro cell line, human xenograft, and mouse allograft preclinical cancer models", Clin Cancer Res. Sep. 15, 2003;9(11):4227-39.
Willner et al., "(6-Maleimidocaproyl)hydrazone of doxorubicin—a new derivative for the preparation of immunoconjugates of doxorubicin", Bioconjug Chem. Nov.-Dec. 1993;4(6):521-7.
Zwirner et al., "MICA, a new polymorphic HLA-related antigen, is expressed mainly by keratinocytes, endothelial cells, and monocytes", Immunogenetics. 1998;47(2)1 39-48.
Chari RV., "Targeted cancer therapy: conferring specificity to cytotoxic drugs", Acc Chem Res. Jan. 2008;41 (1):98-107.

(56) References Cited

OTHER PUBLICATIONS

ClinicalTrials.gov: search for "milatuzumab" (pp. 1-2; Aug. 12, 2013).

Farquhar et al., "Intensely potent doxorubicin analogues: structure-activity relationship", J Med Chem. Mar. 12, 1998;41(6):965-72.

Govindan et al., "Milatuzumab-SN-38 conjugates for the treatment of CD74+ cancers", Mol Cancer Ther. Jun. 2013;12(6):968-78.

Guillemard et al., "Prodrug chemotherapeutics bypass p-glycoprotein resistance and kill tumors in vivo with high efficacy and target-dependent selectivity", Oncogene. Apr. 29, 2004;23(20):3613-21.

Moon et al., "Antibody conjugates of 7-ethyl-10-hydroxycamptothecin (SN-38) for targeted cancer chemotherapy", J Med Chem. Nov. 13, 2008;51(21):6916-26.

Nagy et al., "Cytotoxic analogs of luteinizing hormone-releasing hormone containing doxorubicin or 2-pyrrolinodoxorubicin, a derivative 500-1000 times more potent", Proc Natl Acad Sci U S A. Jul. 9, 1996;93(14):7269-73.

Nagy et al., "Stimulation of macrophage TNFalpha production by orthopaedic wear particles requires activation of the ERK1/2/Egr-1 and NF-kappaB pathways but is independent of p38 and JNK", J Cell Physiol. Dec. 2008;217(3):652-66.

Nagy et al., 'Synthesis and biological evaluation of cytotoxic analogs of somatostatin containing doxorubicin or its intensely potent derivative, 2-pyrrolinodoxorubicin', Proc Natl Acad Sci U S A. Feb. 17, 1998;95(4):1794-9.

Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.

* cited by examiner

FIG. 4
(A)
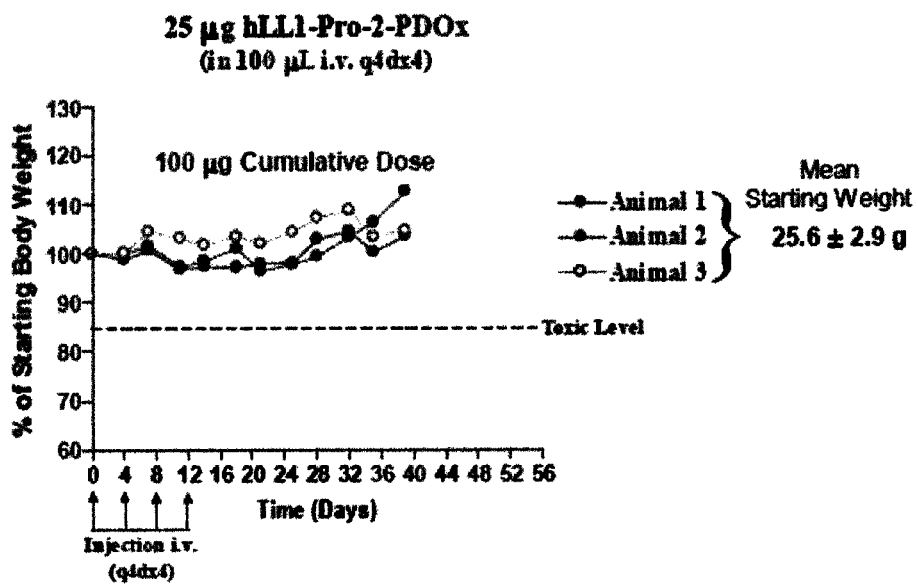
(B)
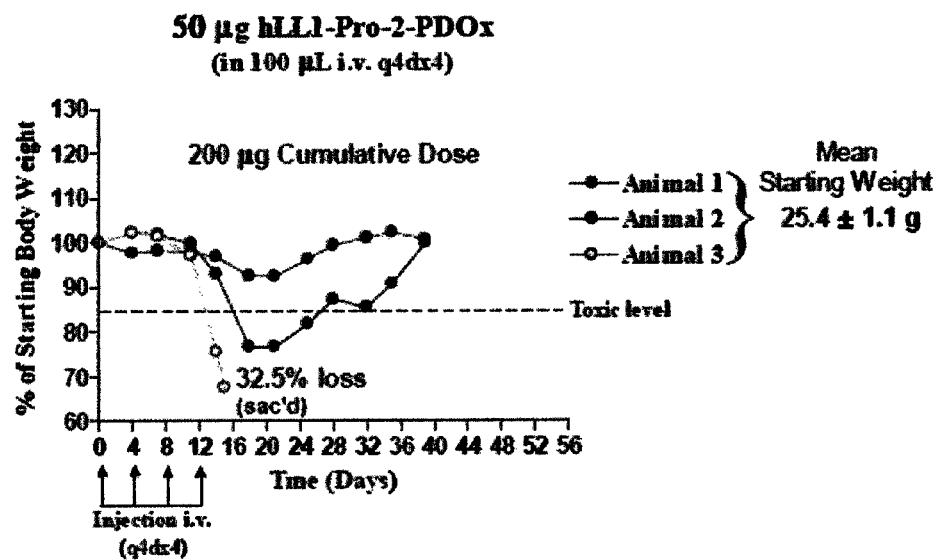

*FIG. 4*
(C)
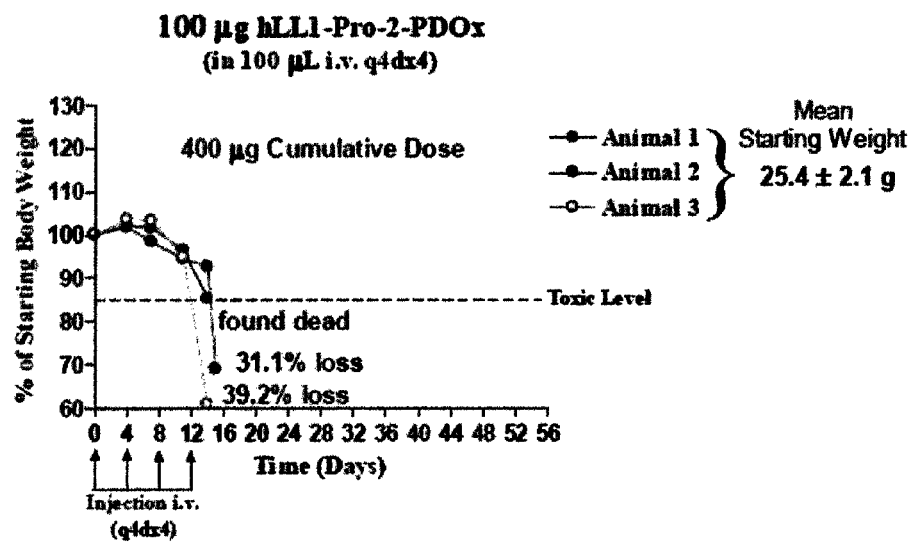
(D)
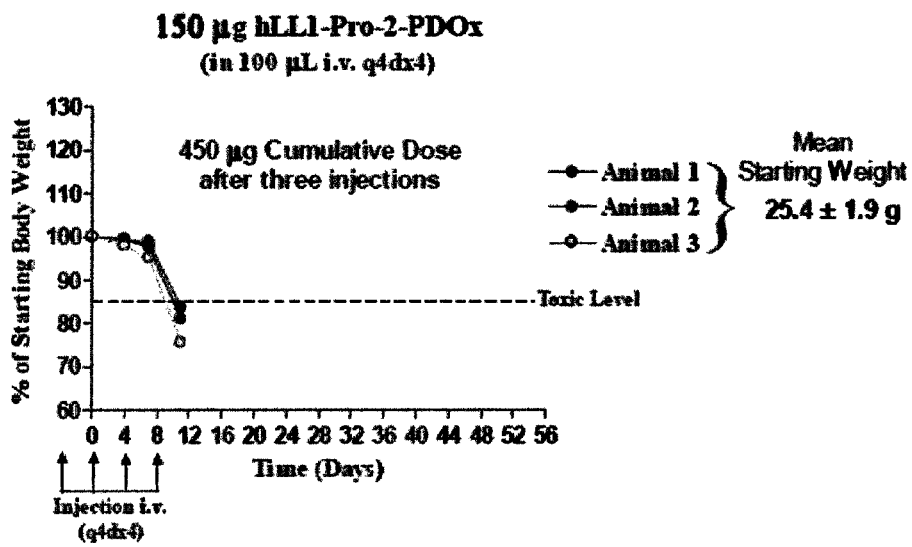

DTPA-Dap-D-Ala-D-Lys(HSG)-D-Ala-D-Lys(HSG)-NH$_2$

SEQUENCE LISTING

```
<160> NUMBER OF SEQ ID NOS: 161

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15
```

```
Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
```

```
                20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Gln
        35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30
```

Val Glu Tyr Phe Thr Arg Leu Arg Glu Ala Arg Ala
            35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

```
Val Glu Tyr Phe Thr Arg Leu Arg Glu Ala Arg Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
```

```
                    20                  25                  30

Val Glu Tyr Phe Thr Arg Leu Arg Glu Ala Arg Ala
            35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15
```

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
            35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
            35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
            35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

```
Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
```

```
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15
Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15
Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15
Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15
Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

-continued

Gln Ile Glu Thr Leu Ala Lys Gln Ile Val Asp Asn Ala Ile Gln Gln
1               5                   10                  15
Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15
Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15
Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15
Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15
Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
                20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
                20

<210> SEQ ID NO 67
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25
```

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

```
                50              55              60
Leu Ser Ser Val Val Thr Val Pro Ser Ser Leu Gly Thr Gln Thr
 65              70              75              80

Tyr Ile Cys Asn Val Asn His Lys Pro Ser Asn Thr Lys Val Asp Lys
                 85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
```

```
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 87

Xaa Xaa Ile Xaa Ile Pro Pro Xaa Leu Xaa Xaa Leu Leu Xaa Xaa Tyr
1               5                   10                  15
```

-continued

```
Xaa Val Xaa Val Leu Xaa Xaa Pro Pro Xaa Leu Val Xaa Phe Xaa
            20                  25                  30

Val Xaa Tyr Phe Xaa Xaa Leu Xaa Xaa Xaa Xaa
        35                  40
```

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

```
Xaa Xaa Xaa Xaa Xaa Ala Xaa Xaa Ile Val Xaa Xaa Ala Ile Xaa Xaa
1               5                   10                  15

Xaa
```

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr

```
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ala Ser Gln Asp Val Ser Ile Ala Val Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 91

Ser Ala Ser Tyr Arg Tyr Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln His Tyr Ile Thr Pro Leu Thr
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asn Tyr Gly Met Asn
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Ile Asn Thr Tyr Thr Gly Glu Pro Thr Tyr Thr Asp Asp Phe Lys
1               5                   10                  15

Gly

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Phe Gly Ser Ser Tyr Trp Tyr Phe Asp Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Ala Ser Gln Asp Val Gly Thr Ser Val Ala
1               5                   10

<210> SEQ ID NO 97
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Thr Ser Thr Arg His Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Ser Leu Tyr Arg Ser
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Tyr Trp Met Ser
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ile His Pro Asp Ser Ser Thr Ile Asn Tyr Ala Pro Ser Leu Lys
1               5                   10                  15

Asp

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Tyr Phe Gly Phe Pro Trp Phe Ala Tyr
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 102

Arg Ser Ser Gln Ser Ile Val His Ser Asn Gly Asn Thr Tyr Leu Glu
1               5                   10                  15

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Val Ser Asn Arg Phe Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Gln Gly Ser His Val Pro Pro Thr
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Tyr Gly Met Asn
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Ile Asn Thr Tyr Thr Gly Glu Pro Thr Tyr Ala Asp Asp Phe Lys
1               5                   10                  15

Gly

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Gly Trp Met Asp Phe Asn Ser Ser Leu Asp Tyr
1               5                   10

<210> SEQ ID NO 108
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ala Ser Ser Arg Val Ser Tyr Ile His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Thr Ser Thr Leu Ala Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Trp Ser Tyr Asn Pro Pro Thr
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Tyr Tyr Met Ser
1               5

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Ile Ala Asn Lys Ala Asn Gly His Thr Thr Asp Tyr Ser Pro Ser
1               5                   10                  15

Val Lys Gly

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 113

Asp Met Gly Ile Arg Trp Asn Phe Asp Val
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ser Ser Gln Ser Leu Val His Arg Asn Gly Asn Thr Tyr Leu His
1               5                   10                  15

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Val Ser Asn Arg Phe Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Gln Ser Ser His Val Pro Pro Thr
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Tyr Gly Val Asn
1               5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Ile Asn Pro Asn Thr Gly Glu Pro Thr Phe Asp Asp Asp Phe Lys
1               5                   10                  15

Gly

<210> SEQ ID NO 119
```

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Arg Gly Lys Asn Glu Ala Trp Phe Ala Tyr
1               5                   10

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Ser Ser Gln Ser Val Leu Tyr Ser Ala Asn His Lys Tyr Leu Ala
1               5                   10                  15

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Ala Ser Thr Arg Glu Ser
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

His Gln Tyr Leu Ser Ser Trp Thr Phe
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Tyr Trp Leu His
1               5

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

```
Tyr Ile Asn Pro Arg Asn Asp Tyr Thr Glu Tyr Asn Gln Asn Phe Lys
1               5                   10                  15
Asp

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Asp Ile Thr Thr Phe Tyr
1               5

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Ser Ser Gln Ser Ile Val His Ser Asn Gly Asn Thr Tyr Leu Glu
1               5                   10                  15

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Lys Val Ser Asn Arg Phe Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Gln Gly Ser Arg Val Pro Tyr Thr
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Tyr Val Ile Thr
1               5

<210> SEQ ID NO 130
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 130

Glu Ile Tyr Pro Gly Ser Gly Ser Thr Ser Tyr Asn Glu Lys Phe Lys
1               5                   10                  15

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Asp Leu
1

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Ala Ser Ser Ser Val Ser Ser Ser Tyr Leu Tyr
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Thr Ser Asn Leu Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

His Gln Trp Asn Arg Tyr Pro Tyr Thr
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Tyr Val Leu His
1               5
```

```
<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Ile Asn Pro Tyr Asn Asp Gly Thr Gln Tyr Asn Glu Lys Phe Lys
1               5                   10                  15

Gly

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Phe Gly Gly Ser Tyr Gly Phe Ala Tyr
1               5                   10

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Tyr Val Ile His
1               5

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Tyr Ile His Pro Tyr Asn Gly Gly Thr Lys Tyr Asn Glu Lys Phe Lys
1               5                   10                  15

Gly

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Gly Gly Gly Asp Pro Phe Ala Tyr
1               5

<210> SEQ ID NO 141
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 141

Lys Ala Ser Gln Asp Ile Asn Lys Tyr Ile Gly
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Thr Ser Ala Leu Leu Pro
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Gln Tyr Asp Asp Leu Trp Thr
1               5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Tyr Gly Met Asn
1               5

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Ile Asn Thr Tyr Thr Arg Glu Pro Thr Tyr Ala Asp Asp Phe Lys
1               5                   10                  15

Gly

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146
```

```
Asp Ile Thr Ala Val Val Pro Thr Gly Phe Asp Tyr
1               5                   10
```

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Arg Ala Ser Glu Asn Ile Tyr Ser Asn Leu Ala
1               5                   10
```

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Ala Ala Ser Asn Leu Ala Asp
1               5
```

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Gln His Phe Trp Thr Thr Pro Trp Ala
1               5
```

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Arg Ala Ser Ser Ser Val Ser Tyr Ile His
1               5                   10
```

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Ala Thr Ser Asn Leu Ala Ser
1               5
```

<210> SEQ ID NO 152
<211> LENGTH: 9
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 152

Gln Gln Trp Thr Ser Asn Pro Pro Thr
1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Tyr Asn Met His
1               5

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ile Tyr Pro Gly Asn Gly Asp Thr Ser Tyr Asn Gln Lys Phe Lys
1               5                   10                  15

Gly

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Thr Tyr Tyr Gly Gly Asp Trp Tyr Phe Asp Val
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Lys Ala Ser Gln Ser Val Asp Tyr Asp Gly Asp Ser Tyr Leu Asn
1               5                   10                  15

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Ala Ser Asn Leu Val Ser
1               5

```
<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Gln Ser Thr Glu Asp Pro Trp Thr
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Tyr Trp Met Asn
1               5

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Ile Trp Pro Gly Asp Gly Asp Thr Asn Tyr Asn Gly Lys Phe Lys
1               5                   10                  15
Gly

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Glu Thr Thr Thr Val Gly Arg Tyr Tyr Tyr Ala Met Asp Tyr
1               5                   10                  15
```

… … …

PRO-DRUG FORM (P2PDOX) OF THE HIGHLY POTENT 2-PYRROLINODOXORUBICIN CONJUGATED TO ANTIBODIES FOR TARGETED THERAPY OF CANCER

RELATED APPLICATIONS

This application claims the benefit under 35 U.S.C. 119(e) of provisional U.S. Patent Application Ser. Nos. 61/761,845, filed Feb. 7, 2013, and 61/810,002 filed Apr. 9, 2013.

SEQUENCE LISTING

The instant application contains a Sequence Listing which has been submitted in ASCII format via EFS-Web and is hereby incorporated by reference in its entirety. Said ASCII copy, created on Feb. 6, 2014, is named IMM341US1_SL.txt and is 60,562 bytes in size.

FIELD OF THE INVENTION

The present invention concerns compositions and methods of production and use of prodrug forms of 2-pyrrolinodoxorubicin (referred to herein as P2PDox). In preferred embodiments, the P2PDox is conjugated to a targeting molecule, preferably an antibody or antigen-binding antibody fragment, a non-antibody cell-targeting construct, or to a targetable construct that binds in vivo to a bispecific antibody that localizes in a target cell, tissue, organ or pathogen. In vivo, the targeted P2PDox is converted to the ultratoxic drug 2-pyrrolinodoxorubicin (2PDox), which has a potent cytotoxic effect on the targeted cell, tissue, organ or pathogen. The antibody-drug conjugate (ADC) formulations are of use for the treatment of a variety of diseases, such as autoimmune disease, immune dysregulation disease, infectious disease, cancer (e.g., carcinoma, sarcoma, melanoma, glioma, neuroblastoma, lymphoma, leukemia, acute and chronic lymphocytic and myelocytic leukemia, follicular lymphoma, diffused large B-cell lymphoma, T-cell lymphoma or leukemia, multiple myeloma or Hodgkin's or non-Hodgkin's lymphoma).

BACKGROUND

Administration of monoclonal antibodies or fragments thereof has been proposed for diagnosis and/or therapy of a wide variety of disease states, such as cancer, infectious diseases, autoimmune or immune dysfunction disease, neurological diseases, cardiovascular disease and metabolic disease. (See, e.g., Nadler et al., 1980, Cancer Res 40:3147-54; Ritz and Schlossman, 1982, Blood 59:1-11; Waldmann, 2003, Nature Med 9:269-77; Ibbotson et al., 2003, Am J Cardiovasc Drugs 3:381-86; Dorner et al., 2009, Nat Rev Rheumatol 5:433-41; Pul et al., 2011, Expert Opin Biol Ther 11:343-57). Human immunoglobulin mixtures are also used, particularly by subcutaneous injection, for the treatment of hepatitis, as well as various autoimmune diseases by intravenous infusion (see, e.g., Powell et al., 2006, Clin Transplant 20:524-25; Stiehm, 1997, Pediatr Infect Dis J 16:696-707; Zandman et al., Clin Rev Allergy Immunol [Epub ahead of print, Jul. 6, 2011]; Kaveri et al., 2011, Clin Exp Immunol 164:2-5).

While naked (unconjugated) antibodies have been successfully used for therapy of cancer and other disease states, the more recent approach has been to use antibody-drug conjugates (ADCs) for targeted therapy of disease. Such conjugates combine the potent cytotoxic effect of conjugated drug with the targeting function (and consequent decrease in systemic toxicity) of antibody or antibody fragment. Various drug conjugates have been developed for ADCs, including camptothecins (e.g., SN-38) (Govindan et al., 2013, Mol Cancer Ther 12:968-78; Sharkey et al., 2011, Mol Cancer Ther 10:1072-81; Moon et al., 2008, J Med Chem 51:6916-26), monomethyl auristatin (Francisco et al., 2003, Blood 102:1458-65; Law et al., 2004, Clin Cancer Res 10:7842-51), calicheamicins (Hinman et al., 1993, Cancer Res 53:3336-42; Gillespie et al., 2000, Ann Oncol 11:735-41; Bross et al., 2001, Clin Cancer Res 7:1490-96) and maytansinoids (Erickson et al., 2006, Cancer Res 66:4426-33; Lewis Phillips et al., 2008, Cancer Res 68:9280-90; Haddley et al., 2013, Drugs Today 49:701-15). However, to date the potential for such compounds remains unfulfilled, and recently the first ADC to receive FDA approval for human use (gemtuzumab ozogamicin) was withdrawn from the market due to increased patient deaths and no added benefit over conventional cancer therapies (Hutter & Schlenk, 2011, Expert Opin Biol Ther 11:1369-80). A need exists for more effective ADCs with lower systemic toxicity and improved therapeutic index.

SUMMARY

The present invention concerns compositions and methods of production and use of conjugates of pro-2-pyrrolinodoxorubicin (P2PDox). Preferably the P2PDox is conjugated to an antibody, antigen-binding antibody fragment, or a targetable construct or other targeting molecule that can deliver the P2PDox to selected target cells, tissues, organs or pathogens. Preferably, the antibody or fragment thereof links to at least one P2PDox; preferably 1 to about 12 P2PDox; more preferably 4 or more P2PDox, most preferably about 6 to about 12 P2PDox moieties. Methods of producing P2PDox, of conjugating P2PDox to antibodies, antibody fragments, peptides or other molecules, and of use of the ADC immunoconjugate are described in more detail below. Preferably, the conjugates are formulated in Good's biological buffers at a pH of 6.0 to 7.0, and lyophilized for storage. Preferably, the Good's buffer is selected from the group consisting of 2-(N-morpholino)ethanesulfonic acid (MES), 3-(N-morpholino)propanesulfonic acid (MOPS), 4-(2-hydroxyethyppiperazine-1-ethanesulfonic acid (HEPES), and 1,4-piperazinediethanesulfonic acid (PIPES), in the pH range of 6-7, preferably in the pH range of 6.5 to 7, and at a buffer concentration of 10-100 mM, preferably 25 mM.

In one embodiment, P2PDox is conjugated to an antibody or other targeting molecule using an acid-cleavable cross-linker. Preferably, P2PDox is conjugated to an antibody, using an acid cleavable linker attached to the thiol groups of interchain disulfide-reduced antibody, providing compositions that are very stable under physiological conditions.

In another preferred embodiment, the preparation of P2PDox, involving reductive alkylation of the amine group on doxorubicin, is carried out in fluorinated solvents such as trifluoroethanol or hexafluoroisopropanol, thereby dissolving the hydrophilic doxorubicin in an organic solvent, and performing reductive alkylation using a mild reducing agent, such as triacetoxyborohydride. This procedure avoids the use of sodium cyanoborohydride, which has the potential drawback of incorporating cyanide in the molecule.

In an alternative embodiment, the process of making P2PDox involves using an excess of aldehyde reagent, a slight molar excess of reducing agent, and diisopropylethylamine as a co-solvent in the fluorinated solvent. This process results in high yields of the product in a short time.

In a further embodiment, P2PDox is converted into the 'activated' form, MCC-P2PDox hydrazone (where MCC is maleimidomethylcyclohexane carbonyl moiety) amenable to antibody conjugation by reacting with a slight molar excess of the commercial SMCC-hydrazide reagent (where SMCC is succinimidyl 4-(N-maleimidomethyl)cyclohexane carboxylate, and the SMCC-hydrazide reagent is the product of SMCC and hydrazine), such that the reaction product is used as such without a need for chromatographic purification.

Antibodies or non-antibody targeting constructs, such as nanobodies, of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD47, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CXCR4, CXCR7, CXCL12, HIF-1α, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, histone H2B, histone H3, histone H4, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, LIVIA (SLC39A6), macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, placental growth factor, p53, PLAGL2, prostatic acid phosphatase, PSA, PRAMS, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-α, Tn antigen, Thomson-Friedenreich antigens, tumor necrosis antigens, TROP-2, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207). Preferably, the antibody binds to CD74, CD20, CD22, HLA-DR, TROP-2, CEACAM5, CEACAM6, AFP or MUC5ac.

Exemplary antibodies that may be utilized include, but are not limited to, hR1 (anti-IGF-1R, U.S. patent application Ser. No. 12/722,645, filed Mar. 12, 2010), hPAM4 (anti-MUC5ac, U.S. Pat. No. 7,282,567), hA20 (anti-CD20, U.S. Pat. No. 7,251,164), hA19 (anti-CD19, U.S. Pat. No. 7,109,304), hIMMU-31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference. More preferably, the antibody is hA20 (veltuzumab), hLL2 (epratuzumab), hLL1 (milatuzumab), hL243 (IMMU-114), IMMU-H2B, IMMU-H3 or IMMU-H4.

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab tiuxetan (anti-CD20), panitumumab (anti-EGFR), rituximab (anti-CD20), tositumomab (anti-CD20), trastuzumab (anti-ErbB2), abagovomab (anti-CA-125), adecatumumab (anti-EpCAM), atlizumab (anti-IL-6 receptor), benralizumab (anti-CD125), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), Benlysta (Human Genome Sciences); antibodies for therapy of Alzheimer's disease such as Alz 50 (Ksiezak-Reding et al., 1987, J Biol Chem 263:7943-47), gantenerumab, solanezumab and infliximab; anti-fibrin antibodies like 59D8, T2G1s, MH1; anti-HIV antibodies such as P4/D10 (U.S. patent application Ser. No. 11/745,692), Ab 75, Ab 76, Ab 77 (Paulik et al., 1999, Biochem Pharmacol 58:1781-90); and antibodies against pathogens such as CR6261 (anti-influenza), exbivirumab (anti-hepatitis B), felvizumab (anti-respiratory syncytial virus), foravirumab (anti-rabies virus), motavizumab (anti-respiratory syncytial virus), palivizumab (anti-respiratory syncytial virus), panobacumab (anti-*Pseudomonas*), rafivirumab (anti-rabies virus), regavirumab (anti-cytomegalovirus), sevirumab (anti-cytomegalovirus), tivirumab (anti-hepatitis B), and urtoxazumab (anti-*E. coli*).

An antibody or antigen-binding fragment of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. Techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As discussed below, techniques for production of human antibodies are also well known.

The therapeutic formulation may comprise an antibody fragment, such as F(ab)$_2$, Fab, scFv, Fv, or a fusion protein utilizing part or all of the light and heavy chains of the F(ab)$_2$, Fab, scFv. The antibody may also be multivalent, or multivalent and multispecific. The antibody may include human constant regions of IgG1, IgG2a, IgG3, or IgG4.

In more preferred embodiments, the allotype of the antibody may be selected to minimize host immunogenic response to the administered antibody, as discussed in more detail below. A preferred allotype is a non-G1m1 allotype (nG1m1), such as G1m3, G1m3,1, G1m-3,2 or G1m-3,1,2. The non-G1m1 allotype is preferred for decreased antibody immunoreactivity. Surprisingly, repeated subcutaneous administration of concentrated nG1m1 antibody was not found to induce significant immune response, despite the enhanced immunogenicity of subcutaneous administration.

Various embodiments may concern use of the subject methods and compositions to treat a disease, including but not limited to non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas, melanomas, sarcomas, gliomas, and skin cancers. The carcinomas may include carcinomas of the oral cavity, thyroid, gastrointestinal tract, pulmonary tract, lung, breast, ovary, prostate, uterus, endometrium, cervix, urinary bladder, pancreas, bone, brain, connective tissue, liver, gall bladder, kidney, skin, central nervous system, endocrine organs, and testes.

In addition, the subject methods and compositions may be used to treat an autoimmune disease, for example acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis. In other embodiments, the subject methods and compositions may be used to treat immune dysregulatory diseases, such as graft-versus-host disease or organ transplant rejection.

In certain embodiments, disease therapy may be enhanced by combination therapy with one or more other therapeutic agents as part of this invention. Known therapeutic agents of use in this invention include immunomodulators (such as cytokines, lymphokines, chemokines, and growth factors, and their inhibitors), sphingosine inhibitors, hormones, hormone antagonists, oligonucleotides (such as siRNA or RNAi), photoactive therapeutic agents, anti-angiogenic agents and pro-apoptotic agents. Other more traditional therapeutic agents, such as cytotoxic drugs or radionuclides, may be administered before, concurrently with, or after the P2PDox-antibody conjugate.

Preferred optimal dosing of immunoconjugates may include a dosage, in a 70 kg adult, of between 0.3 mg/kg and 5 mg/kg, preferably given either weekly, every other week, or less frequently, such as once every 3 weeks. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. The dosage may be up to 5 mg/kg. Exemplary dosages of use may include 0.3 mg/kg, 0.5 mg/kg, 0.7 mg/kg, 1.0 mg/kg, 1.2 mg/kg, 1.5 mg/kg, 2.0 mg/kg, 2.5 mg/kg, 3.0 mg/kg, 3.5 mg/kg, 4.0 mg/kg, 4.5 mg/kg and 5.0 mg/kg. Preferred dosages are 0.6 mg/kg for weekly administration and 1.2 mg/kg for less frequent dosing. The person of ordinary skill will realize that a variety of factors, such as age, general health, specific organ function or weight, as well as effects of prior therapy on specific organ systems (e.g., bone marrow) may be considered in selecting an optimal dosage of immunoconjugate, and that the dosage and/or frequency of administration may be increased or decreased during the course of therapy. The dosage may be repeated as needed, with evidence of tumor shrinkage observed after as few as 3 to 8 doses. Dosages for pediatric patients who are smaller than 70 kg or 1.7 m are adjusted according to usual pediatric practice.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 4A. MTD study of hLL1-P2PDox conjugates with multiple injections. Mice administered hLL1-P2PDox (q4dx4) at 25 μg i.v. per dose.

FIG. 4B. MTD study of hLL1-P2PDox conjugates with multiple injections. Mice administered hLL1-P2PDox (q4dx4) at 50 μg i.v. per dose.

FIG. 4C. MTD study of hLL1-P2PDox conjugates with multiple injections. Mice administered hLL1-P2PDox (q4dx4) at 100 µg i.v. per dose.

FIG. 4D. MTD study of hLL1-P2PDox conjugates with multiple injections. Mice administered hLL1-P2PDox (q4dx4) at 150 µg i.v. per dose.

DETAILED DESCRIPTION

Definitions

Figure 1:
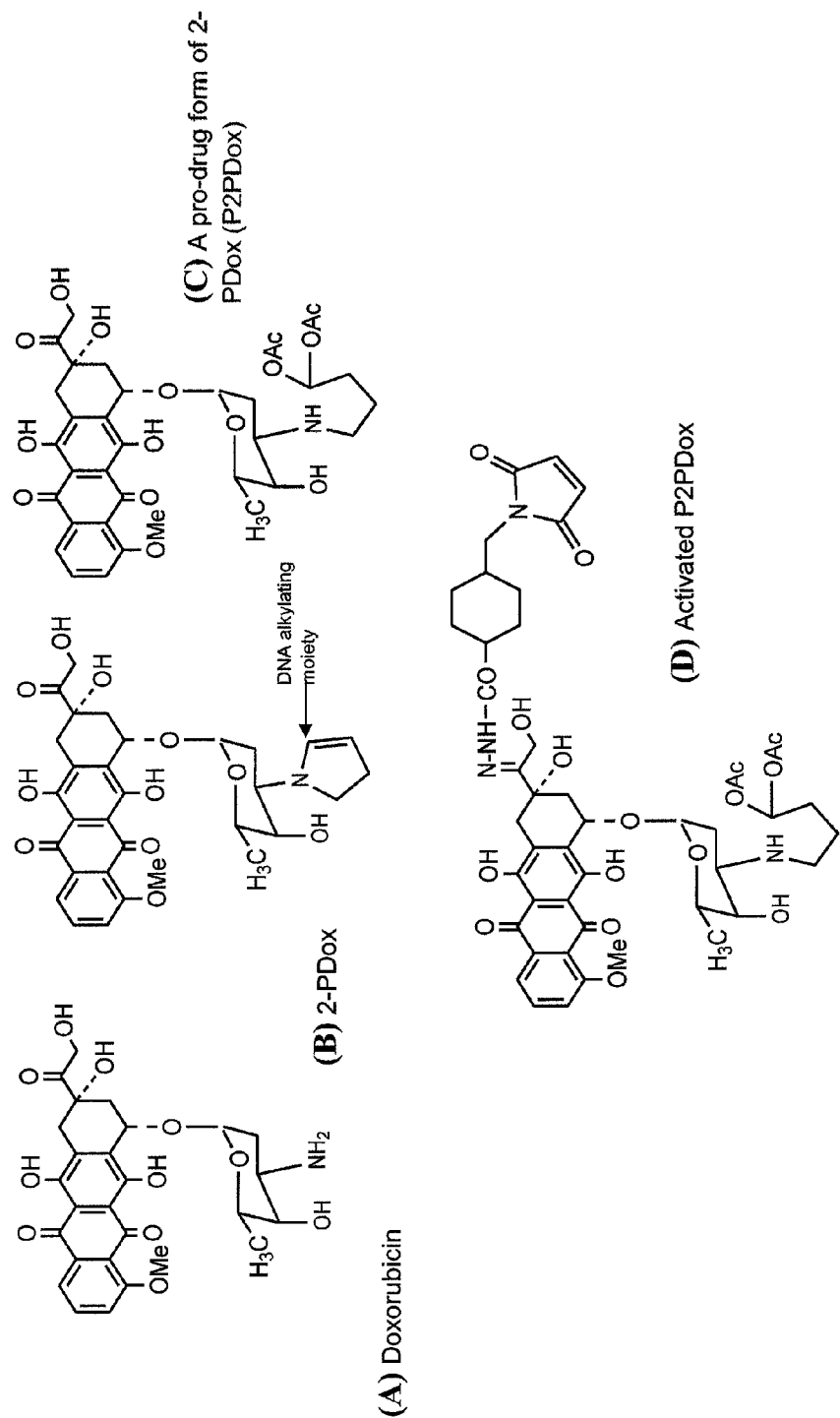
FIG. 1A. Structure of doxorubicin. "Me" is a methyl group.
FIG. 1B. Structure of 2-pyrrolinodoxorubicin,(2-PDox). "Me" is a methyl group.
FIG. 1C. Structure of a prodrug form of 2-pyrrolinodoxorubicin, (P2PDox). "Me" is a methyl group and "Ac" is an acetyl group.
FIG. 1D. Structure of a maleimide-activated form of P2PDox, for antibody coupling. "Me" is a methyl group and "Ac" is an acetyl group.

The following definitions are provided to facilitate understanding of the disclosure herein. Where a term is not specifically defined, it is used in accordance with its plain and ordinary meaning.

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al., 2007, Science 317: 1554-1557). Regardless of structure, an antibody fragment binds with the same antigen that is recognized by the intact antibody. For example, an anti-CD74 antibody fragment binds with an epitope of CD74. The term "antibody fragment" also includes isolated fragments consisting of the variable regions, such as the "Fv" fragments consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229, 275).

A "therapeutic agent" is an atom, molecule, or compound that is useful in the treatment of a disease. Examples of therapeutic agents include but are not limited to antibodies, antibody fragments, drugs, cytokine or chemokine inhibitors, nanobodies, proapoptotic agents, tyrosine kinase inhibitors, toxins, enzymes, nucleases, hormones, immunomodulators, antisense oligonucleotides, siRNA, RNAi, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody with an atom, molecule, or a higher-ordered structure (e.g., with a liposome), a therapeutic agent, or a diagnostic agent. A "naked antibody" is an antibody that is not conjugated to any other agent.

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it, has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a B cell, T cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering.

A "nanobody" (single-domain antibody) is an antibody fragments consisting of a single monomeric variable antibody domain. Like antibodies, nanobodies are capable of selective binding to a specific antigen. With a typical molecular weight of 12-15 kDa, nanobodies are substantially smaller than antibodies.

Pro-2-Pyrrolinodoxorubicin (P2PDox)

The antibody-drug conjugate (ADC) approach to cancer therapy is a topic of considerable current interest (Chari, 2008, Acc Chem Res 41:98-107), especially in view of the recent FDA approvals for products for Hodgkin lymphoma and HER2+ metastatic breast cancer (Deng et al., 2013, Clin Cancer Res 19:22-7; Peddi & Hurvitz, 2013, Future Oncol 9:319-26). With ultratoxic drug-based ADCs, the total patient dose, and the cost of therapeutic agent, will be less. However, the ADC design should be optimized to achieve objective responses.

There are practical aspects to consider in selecting an ultratoxic drug: (i) The commercial availability of the drug in the cGMP grade; (ii) facile preparation of the activated form of the drug, incorporating a cleavable linker and a MAb-conjugating group; and (iii) safety considerations in handling the material. We decided on 2-pyrrolinodoxorubicin for the present ADCs. This drug was described first in 1996 by Schally's group, who later used it for conjugating to a number of receptor-targeted peptides for preclinical explorations (Nagy et al., 1996a, Proc Natl Acad Sci USA 93:7269-73; Nagy et al., 1996b, Proc Natl Acad Sci USA 93:2464-9; Nagy et al., 1997, Proc Natl Acad Sci USA 94:652-6; Nagy et al., 1998, Proc Natl Acad Sci USA 95:1794-9). This is a derivative of doxorubicin, with the daunosamine nitrogen incorporated into a 5-membered enamine, making it a highly potent alkylating agent, with cytotoxicity 500-1000 times that of doxorubicin. The drug's ultratoxicity necessitates special handling in isolators, for safety.

A prodrug form of 2-pyrrolinodoxorubicin was investigated by another group, who disclosed a derivative of doxorubicin, namely N-(4,4-diacetoxybutyl)doxorubicin (Farquhar et al., 1998, J Med Chem 41:965-72; U.S. Pat. Nos.

5,196,522; 6,433,150), which is convertible to 2-pyrrolinodoxorubicin in vivo. This derivative was prepared by reductive alkylation of doxorubicin with 4,4-diacetoxybutyraldehyde. However, this prodrug was not attached to an antibody or other targeting molecule using an acid-labile group, such as hydrazone, as the cleavable linker, at the thiols of disulfide-reduced antibodies.

The studies disclosed in the Examples below use pro-2-pyrrolinodoxorubicin (P2PDox) as the drug in the ADC. There are several advantages to this: (i) handling only the prodrug, thereby mitigating safety concerns; (ii) the raw material doxorubicin (Dox) is available in quantity in the cGMP grade; and (iii) the chemistry of converting Dox to activated P2PDox (P2PDox) involves only a few synthetic steps. FIG. 1A-1D shows the structures of Dox, 2-PDox, P2PDox (P2PDox), and activated P2PDox. For coupling to IgG, we activated P2PDox with SMCC-hydrazide, a procedure that introduces acid-labile hydrazone as well as the maleimide group, the latter for conjugation to thiols of mildly reduced antibody.

The choice of 2-pyrrolinodoxorubicin as the ultratoxic drug, particularly its prodrug form for conjugation to MAbs, enables rapid immunoconjugate development, as the raw material doxorubicin is readily available in the cGMP grade. The ketone on P2PDox provides a handle to incorporate acid-labile hydrazone and antibody-binding maleimide groups in a single step. The derivatization of the amino group of the doxorubicin in the 2-PDox version should overcome multi-drug resistance associated with doxorubicin, based on literature precedents (Farquhar et al., 1998, 41:965-72; Guillemard & Uri, 2004, Oncogene 23:3613-21). The design provides an option to add hydrophilic groups into the linker or N-alkyl portion, if desired, for radiolabeling purpose and/or further modulating administrable dose, without affecting the active 2-pyrrolinodoxorubicin structure that is generated in vivo.

Most of the ADCs currently being examined by others incorporate tubulin-acting, ultratoxic, maytansinoids and auristatins, which are cell-cycle-phase-specific. Anecdotally, except for trastuzumab-DM1, these ADCs appear to exhibit a relatively narrow therapeutic index clinically in solid cancers. A DNA-alkylating agent, such as 2-PDox, is cell-cycle-phase-nonspecific. The proposed ADC, based on a drug component that acts by a different mechanism of cell-killing, an internalizing antibody that shows greater cancer specificity than many others, such as EpCAM MAbs, and the chemistry of linking, offers a departure from other ultratoxic ADCs, and provides an improved therapeutic index. As shown below, preclinical studies conducted to date in aggressive xenograft models of pancreatic, breast, and gastric cancers show the hRS7-P2PDox conjugate to be very active at low and safe doses, leading to complete regressions. Studies in mice bearing human hematological and solid tumors treated with a variety of antibodies targeting such tumors and conjugated with P2PDox also show excellent tumor control (retardation or regression of growth, as compared to control groups), even at infrequent doses, with dose-limiting toxicities due mostly to neutropenia, which is controlled by adjusting the doses to be lower than the maximal tolerated dose (MTD), usually a dose that results in 5% or less mortality.

Preparation of Monoclonal Antibodies

The compositions, formulations and methods described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

Chimeric Antibodies

A chimeric antibody is a recombinant protein that contains the variable domains including the CDRs derived from one species of animal, such as a rodent antibody, while the remainder of the antibody molecule; i.e., the constant domains, is derived from a human antibody. Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and $IgG_1$ constant region domains. This publication also provides the nucleotide sequences of the LL2 light and heavy chain variable regions, $V_k$ and $V_H$, respectively.

Humanized Antibodies

A chimeric monoclonal antibody can be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

Human Antibodies

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., Molecular Cloning, A laboratory manual, 2$^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human antibody. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., Cancer, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown below for the exemplary antibodies rituximab (SEQ ID NO:85) and veltuzumab (SEQ ID NO:86).

```
Rituximab heavy chain variable region sequence
                                      (SEQ ID NO: 85)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKA

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

Veltuzumab heavy chain variable region
                                      (SEQ ID NO: 86)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m-1,2 allotype was characterized by glutamic acid at Kabat position 356, methionine at Kabat position 358 and alanine at Kabat position 431. The G1m-1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km-1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | |
|---|---|---|---|---|---|
| | Complete allotype | 214 (allotype) | | 356/358 (allotype) | 431 (allotype) |
| Rituximab | G1m17,1 | K | 17 | D/L  1 | A  — |
| Veltuzumab | G1m3 | R | 3 | E/M  — | A  — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m-1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282, 567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206;

6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful antigens that may be targeted using the described conjugates include carbonic anhydrase IX, B7, CCCL19, CCCL21, CSAp, HER-2/neu, BrE3, CD1, CD11a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX), ErbB2, ErbB3, Factor H, FHL-1, Flt-3, folate receptor, Ga 733, GRO-β, HMGB-1, hypoxia inducible factor (HIF), HM1.24, HER-2/neu, histone H2B, histone H3, histone H4, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, PD-L1, NCA-95, NCA-90, A3, A33, Ep-CAM, KS-i, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375:51-9).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection (Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, *Diabetes* 45:881-85); murine antibodies MTNFα1, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Checkpoint inhibitor antibodies have been used primarily in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD 1, also known as CD279) and programmed cell death 1 ligand 1 (PD-L1, also known as CD274), may be used in combination with one or more other agents to enhance the effectiveness of immune response against disease cells, tissues or pathogens. Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM® (AB137132), BIOLEGEND® (EH 12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

Type-1 and Type-2 diabetes may be treated using known antibodies against B-cell antigens, such as CD22 (epratuzumab and hRFB4), CD74 (milatuzumab), CD19 (hA19), CD20 (veltuzumab) or HLA-DR (hL243) (see, e.g., Winer et al., 2011, *Nature Med* 17:610-18). Anti-CD3 antibodies also have been proposed for therapy of type-1 diabetes (Cernea et al., 2010, *Diabetes Metab Rev* 26:602-05).

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., *Immunology* 98:296-302 (1999)). A review of the use of CD74 antibodies in cancer is contained in Stein et al., *Clin Cancer Res.* 2007 Sep. 15; 13(18 Pt 2):5556s-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz, cited above. A review listing antibodies against infectious organisms (antitoxin and antiviral antibodies), as well as other targets, is contained in Casadevall, *Clin Immunol* 1999; 93(1):5-15, incorporated herein by reference.

In a preferred embodiment, the pathogens are selected from the group consisting of HIV virus, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, Hemophilis influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416, the Examples section of which is incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target*, 5:75-91, 1998). Attempts at treating HIV infection in AIDS patients failed, possibly due to insufficient efficacy or unacceptable host toxicity. The CPT drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the P4/D10 anti-envelope antibody described by Johansson et al. (*AIDS*. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., *AIDS* 2007; 21(16):2161-2170 and Joos et al., *Antimicrob. Agents Chemother.* 2006; 50(5): 1773-9, all incorporated herein by reference. A preferred targeting agent for HIV is various combinations of these antibodies in order to overcome resistance.

Antibodies of use to treat autoimmune disease or immune system dysfunctions (e.g., graft-versus-host disease, organ transplant rejection) are known in the art and may be conjugated to P2PDox using the disclosed methods and compositions. Antibodies of use to treat autoimmune/immune dysfunction disease may bind to exemplary antigens including, but not limited to, BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, TNF-alpha, interferon, IL-6 and HLA-DR. Antibodies that bind to these and other target antigens, discussed above, may be used to treat autoimmune or immune dysfunction diseases. Autoimmune diseases that may be treated with immuno conjugates may include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

The antibodies discussed above and other known antibodies against disease-associated antigens may be used as P2PDox-conjugates, in the practice of the claimed methods and compositions.

Antibody Fragments

Antibody fragments which recognize specific epitopes can be generated by known techniques. The antibody fragments are antigen binding portions of an antibody, such as $F(ab)_2$, Fab', Fab, Fv, scFv and the like. Other antibody fragments include, but are not limited to: the $F(ab')_2$ fragments which can be produced by pepsin digestion of the antibody molecule and the Fab' fragments, which can be generated by reducing disulfide bridges of the $F(ab')_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Homick et al., 2000, J Nucl Med 41:355-62; Hinton et al., 2006, J Immunol 176:346-56; Petkova et al. 2006, Int Immunol 18:1759-69; U.S. Pat. No. 7,217,797; Hwang and Foote, 2005, Methods 36:3-10; Clark, 2000, Immunol Today 21:397-402; J Immunol 1976 117: 1056-60; Ellison et al., 1982, Nucl Acids Res 13:4071-79; Stickler et al., 2011, Genes and Immunity 12:213-21).

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). A preferred bispecific antibody is an anti-CD3 X anti-CD19 antibody. In alternative embodiments, an anti-CD3 antibody or fragment thereof may be attached to an antibody or fragment against another B-cell associated antigen, such as anti-CD3 X anti-CD20, anti-CD3 X anti-CD22, anti-CD3 X anti-HLA-DR or anti-CD3 X anti-CD74. In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature, 1985; 314:628-631; Perez, et al. Nature, 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens.

DOCK-AND-LOCK™ (DNL™)

In preferred embodiments, a bivalent or multivalent antibody is formed as a DOCK-AND-LOCK™ (DNL™) complex (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters*. 2005; 579: 3264. Wong and Scott, *Nat. Rev. Mol. Cell. Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., *J. Biol. Chem.* 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (RI and RII), and each type has α and β isoforms (Scott, *Pharmacol. Ther.* 1991; 50:123). Thus, the four isoforms of PKA regulatory subunits are RIα, RIα, RIIα and RIIβ. The R subunits have been isolated only as stable dimers and the dimerization domain has been shown to consist of the first 44 amino-terminal residues of RIIα (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci. USA*. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell. Biol.* 2004; 5:959). The AD of AKAPs for PKA is an amphipathic helix of 14-18 residues (Carr et al., *J. Biol. Chem.* 1991; 266:14188). The amino acid sequences of the AD are quite varied among individual AKAPs, with the binding affinities reported for RII dimers ranging from 2 to 90 nM (Alto et al., *Proc. Natl. Acad. Sci. USA*. 2003; 100:4445). AKAPs will only bind to dimeric R subunits. For human RIIα, the AD binds to a hydrophobic surface formed by the 23 amino-terminal residues (Colledge and Scott, *Trends Cell Biol.* 1999; 6:216). Thus, the dimerization domain and AKAP binding domain of human RIIα are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA*. 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature, and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., *Molecular Cloning, A laboratory manual*, 2nd Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In various embodiments, an antibody or antibody fragment may be incorporated into a DNL™ complex by, for example, attaching a DDD or AD moiety to the C-terminal end of the antibody heavy chain, as described in detail below. In more preferred embodiments, the DDD or AD moiety, more preferably the AD moiety, may be attached to the C-terminal end of the antibody light chain (see, e.g., U.S. patent application Ser. No. 13/901,737, filed May 24, 2013, the Examples section of which is incorporated herein by reference.)

Structure-Function Relationships in AD and DDD Moieties

For different types of DNL™ constructs, different AD or DDD sequences may be utilized. Exemplary DDD and AD sequences are provided below.

```
DDD1
                                              (SEQ ID NO: 1)
SHIQIPPGLTELLQGYTVEVLRQQPPDLVEFAVEYFTRLREARA

DDD2
                                              (SEQ ID NO: 2)
CGHIQIPPGLTELLQGYTVEVLRQQPPDLVEFAVEYFTRLREARA

AD1
                                              (SEQ ID NO: 3)
QIEYLAKQIVDNAIQQA

AD2
                                              (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                              (SEQ ID NO: 5)
SLRECELYVQKHNIQALLKDSIVQLCTARPERPMAFLREYFERLEKEEAK

DDD3C
                                              (SEQ ID NO: 6)
MSCGGSLRECELYVQKHNIQALLKDSIVQLCTARPERPMAFLREYFERLE
KEEAK

AD3
                                              (SEQ ID NO: 7)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                              (SEQ ID NO: 8)
SLRECELYVQKHNIQALLKDVSIVQLCTARPERPMAFLREYFEKLEKEE
AK

PKA RIβ
                                              (SEQ ID NO: 9)
SLKGCELYVQLHGIQQVLKDCIVHLCISKPERPMKFLREHFEKLEKEEN
RQILA

PKA RIIα
                                              (SEQ ID NO: 10)
SHIQIPPGLTELLQGYTVEVGQQPPDLVDFAVEYFTRLREARRQ

PKA RIIβ
                                              (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, *Protein Sci* 14:2982-92; Carr et al., 2001, *J Biol Chem* 276:17332-38; Alto et al., 2003, *Proc Natl Acad Sci USA* 100:4445-50; Hundsrucker et al., 2006, *Biochem J* 396:297-306; Stokka et al., 2006, *Biochem J* 400: 493-99; Gold et al., 2006, *Mol Cell* 24:383-95; Kinderman et al., 2006, *Mol Cell* 24:397-408, the entire text of each of which is incorporated herein by reference.)

For example, Kinderman et al. (2006, *Mol Cell* 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                              (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, *Proc Natl Acad Sci USA* 100:4445-50).

TABLE 2

Conservative Amino Acid Substitutions in DDD1 (SEQ ID NO: 1). Consensus sequence disclosed as SEQ ID NO: 87.

| S | H | <u>I</u> | Q | <u>I</u> | P | P | G | <u>L</u> | T | E | <u>L</u> | <u>L</u> | Q | G | <u>Y</u> | T | <u>V</u> | E | <u>V</u> | <u>L</u> | R |
|---|---|---|---|---|---|---|---|---|---|---|---|---|---|---|---|---|---|---|---|---|---|
| T | K<br>R | | N | | | | A | | S | D | | | N | A | | S | | D | | | K |
| Q | Q | P | P | D | <u>L</u> | <u>V</u> | E | <u>F</u> | A | <u>V</u> | E | <u>Y</u> | <u>F</u> | T | R | <u>L</u> | R | E | A | R | A |
| N | N | | | E | | | D | | L<br>I<br>V | | D | | | S | K | | K | D | L<br>I<br>V | K | L<br>I<br>V |

THIQIPPGLTELLQGYTVEVLRQQPPDLVEFAVEYFTRLREARA
(SEQ ID NO: 12)

SKIQIPPGLTELLQGYTVEVLRQQPPDLVEFAVEYFTRLREARA
(SEQ ID NO: 13)

SRIQIPPGLTELLQGYTVEVLRQQPPDLVEFAVEYFTRLREARA
(SEQ ID NO: 14)

SHINIPPGLTELLQGYTVEVLRQQPPDLVEFAVEYFTRLREARA
(SEQ ID NO: 15)

SHIQIPPALTELLQGYTVEVLRQQPPDLVEFAVEYFTRLREARA
(SEQ ID NO: 16)

SHIQIPPGLSELLQGYTVEVLRQQPPDLVEFAVEYFTRLREARA
(SEQ ID NO: 17)

SHIQIPPGLTDLLQGYTVEVLRQQPPDLVEFAVEYFTRLREARA
(SEQ ID NO: 18)

SHIQIPPGLTELLNGYTVEVLRQQPPDLVEFAVEYFTRLREARA
(SEQ ID NO: 19)

SHIQIPPGLTELLQAYTVEVLRQQPPDLVEFAVEYFTRLREARA
(SEQ ID NO: 20)

SHIQIPPGLTELLQGYSVEVLRQQPPDLVEFAVEYFTRLREARA
(SEQ ID NO: 21)

SHIQIPPGLTELLQGYTVDVLRQQPPDLVEFAVEYFTRLREARA
(SEQ ID NO: 22)

SHIQIPPGLTELLQGYTVEVLKQQPPDLVEFAVEYFTRLREARA
(SEQ ID NO: 23)

SHIQIPPGLTELLQGYTVEVLRNQPPDLVEFAVEYFTRLREARA
(SEQ ID NO: 24)

SHIQIPPGLTELLQGYTVEVLRQNPPDLVEFAVEYFTRLREARA
(SEQ ID NO: 25)

SHIQIPPGLTELLQGYTVEVLRQQPPELVEFAVEYFTRLREARA
(SEQ ID NO: 26)

SHIQIPPGLTELLQGYTVEVLRQQPPDLVDFAVEYFTRLREARA
(SEQ ID NO: 27)

SHIQIPPGLTELLQGYTVEVLRQQPPDLVEFLVEYFTRLREARA
(SEQ ID NO: 28)

SHIQIPPGLTELLQGYTVEVLRQQPPDLVEFIVEYFTRLREARA
(SEQ ID NO: 29)

SHIQIPPGLTELLQGYTVEVLRQQPPDLVEFVVEYFTRLREARA
(SEQ ID NO: 30)

SHIQIPPGLTELLQGYTVEVLRQQPPDLVEFAVDYFTRLREARA
(SEQ ID NO: 31)

Alto et al. (2003, *Proc Natl Acad Sci USA* 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:3), similar to that shown for DDD1 (SEQ ID NO:1) in Table 2 above.

A limited number of such potential alternative AD moiety sequences are shown in SEQ ID NO:32 to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

```
            AKAP-IS
                                     (SEQ ID NO: 3)
            QIEYLAKQIVDNAIQQA
```

TABLE 3

Conservative Amino Acid Substitutions in AD1(SEQ ID NO: 3). Consensus sequence disclosed as SEQ ID NO: 88.

| Q | I | E | Y | L | A | K | Q | I V | D | N | A | I Q | Q | A |
|---|---|---|---|---|---|---|---|-----|---|---|---|-----|---|---|
| N | L | D | F | I |   | R | N |     | E | Q |   |     | N | N | L |
|   | V |   | T | V |   |   |   |     |   |   |   |     |   |   | I |
|   |   |   | S |   |   |   |   |     |   |   |   |     |   |   | V |

NIEYLAKQIVDNAIQQA (SEQ ID NO: 32)

QLEYLAKQIVDNAIQQA (SEQ ID NO: 33)

QVEYLAKQIVDNAIQQA (SEQ ID NO: 34)

QIDYLAKQIVDNAIQQA (SEQ ID NO: 35)

QIEFLAKQIVDNAIQQA (SEQ ID NO: 36)

QIETLAKQIVDNAIQQA (SEQ ID NO: 37)

QIESLAKQIVDNAIQQA (SEQ ID NO: 38)

QIEYIAKQIVDNAIQQA (SEQ ID NO: 39)

QIEYVAKQIVDNAIQQA (SEQ ID NO: 40)

QIEYLARQIVDNAIQQA (SEQ ID NO: 41)

QIEYLAKNIVDNAIQQA (SEQ ID NO: 42)

QIEYLAKQIVENAIQQA (SEQ ID NO: 43)

QIEYLAKQIVDQAIQQA (SEQ ID NO: 44)

QIEYLAKQIVDNAINQA (SEQ ID NO: 45)

QIEYLAKQIVDNAIQNA (SEQ ID NO: 46)

QIEYLAKQIVDNAIQQL (SEQ ID NO: 47)

TABLE 3-continued

Conservative Amino Acid Substitutions in AD1(SEQ ID NO: 3). Consensus sequence disclosed as SEQ ID NO: 88.

QIEYLAKQIVDNAIQQI (SEQ ID NO: 48)

QIEYLAKQIVDNAIQQV (SEQ ID NO: 49)

Gold et al. (2006, *Mol Cell* 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIM were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

```
            SuperAKAP-IS
                                     (SEQ ID NO: 50)
            QIEYVAKQIVDYAIHQA Alternative AKAP sequences
                                     (SEQ ID NO: 51)
            QIEYKAKQIVDHAIHQA (SEQ ID NO: 52)
            QIEYHAKQIVDHAIHQA (SEQ ID NO: 53)
            QIEYVAKQIVDHAIHQA
```

Figure 2:
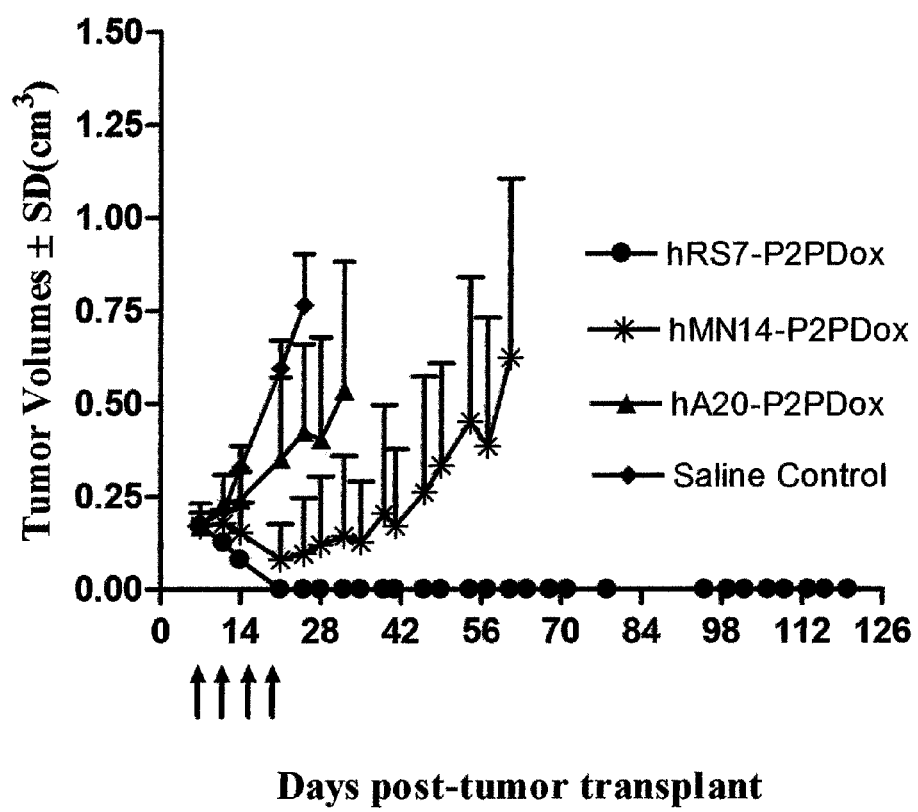
FIG. 2. Therapy in nude mice bearing s.c. human tumor xenografts using 2.25 mg/kg protein dose (0.064 mg/kg of drug dose) of MAb-P2PDox conjugates twice weekly×2 weeks in nude mice with Capan-1 human pancreatic adenocarcinoma xenografts (n=5).

FIG. 2 of Gold et al. disclosed additional DDD-binding sequences from a variety of AKAP proteins, shown below.

```
            RII-Specific AKAPs
            AKAP-KL
                                     (SEQ ID NO: 54)
            PLEYQAGLLVQNAIQQAI AKAP79
                                     (SEQ ID NO: 55)
            LLIETASSLVKNAIQLSI AKAP-Lbc
                                     (SEQ ID NO: 56)
            LIEEAASRIVDAVIEQVK RI-Specific AKAPs
            AKAPce
                                     (SEQ ID NO: 57)
            ALYQFADRFSELVISEAL RIAD
                                     (SEQ ID NO: 58)
            LEQVANQLADQIIKEAT
```

PV38
(SEQ ID NO: 59)
FEELAWKIAKMIWSDVF

Dual-Specificity AKAPs
AKAP7
(SEQ ID NO: 60)
ELVRLSKRLVENAVLKAV

MAP2D
(SEQ ID NO: 61)
TAEEVSARIVQVVTAEAV

DAKAP1
(SEQ ID NO: 62)
QIKQAAFQLISQVILEAT

DAKAP2
(SEQ ID NO: 63)
LAWKIAKMIVSDVMQQ

Stokka et al. (2006, *Biochem J* 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

Ht31
(SEQ ID NO: 64)
DLIEEAASRIVDAVIEQVKAAGAY

RIAD
(SEQ ID NO: 65)
LEQYANQLADQIIKEATE

PV-38
(SEQ ID NO: 66)
FEELAWKIAKMIWSDVFQQC

Hundsrucker et al. (2006, *Biochem J* 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

| AKAP Peptide sequences | |
|---|---|
| | Peptide Sequence |
| AKAPIS | QIEYLAKQIVDNAIQAA (SEQ ID NO: 3) |
| AKAPIS-P | QIEYLAKQIPDNAIQAA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |

TABLE 4-continued

| AKAP Peptide sequences | |
|---|---|
| | Peptide Sequence |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP 10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
(SEQ ID NO: 3)
QIEYL<u>AKQIVDNAIQQ</u>A

Carr et al. (2001, *J Biol Chem* 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SH*IQIPP*GLT*ELLQG*Y*T*V*EVLRQQPP*DLVEFA*VE*YF*TR*LR*EARA

A modified set of conservative amino acid substitutions for the DDD1 (SEQ ID NO:1) sequence, based on the data of Carr et al. (2001) is shown in Table 5. Even with this reduced set of substituted sequences, there are numerous possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 1). Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   |   | N |   |   |   |   |   | S |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   |   |   |   |   | I | D |   |   | S | K |   | K |   | L |   | L |
|   |   |   |   |   |   |   |   |   |   | L |   |   |   |   |   |   |   |   | I |   | I |
|   |   |   |   |   |   |   |   |   |   | A |   |   |   |   |   |   |   |   | V |   | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, *J. Mol. Biol.*, 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry*, 13:222-245; 1978, *Ann. Rev. Biochem.*, 47: 251-276; 1979, *Biophys. J.*, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gin, asn, lys; Asn (N) his, asp, lys, arg, gin; Asp (D) asn, glu; Cys (C) ala, ser; Gln (Q) glu, asn; Glu (E) gin, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, *Nat. Biotechnol.* 23:1493-94; Silverman et al., 2006, *Nat. Biotechnol.* 24:220). The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference. Avimers may be conjugated to P2PDox using the methods and compositions disclosed herein.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, *Science* 228:1315-1317; Smith and Scott, 1993, *Meth. Enzymol.* 21:228-257). In addition to peptides, larger protein domains such as single-chain antibodies may also be displayed on the surface of phage particles (Arap et al., 1998, *Science* 279:377-380).

Targeting amino acid sequences selective for a given organ, tissue, cell type or target molecule may be isolated by panning (Pasqualini and Ruoslahti, 1996, *Nature* 380:364-366; Pasqualini, 1999, *The Quart. J. Nucl. Med.* 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807. Phage display peptides may be conjugated to P2PDox using the methods and compositions disclosed herein.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. No. 5,475,096 and U.S. Pat. No. 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical. Aptamers may be conjugated to P2PDox using the methods and compositions disclosed herein.

Affibodies and Fynomers

Certain alternative embodiments may utilize affibodies in place of antibodies. Affibodies are commercially available from Affibody AB (Solna, Sweden). Affibodies are small proteins that function as antibody mimetics and are of use in binding target molecules. Affibodies were developed by combinatorial engineering on an alpha helical protein scaffold (Nord et al., 1995, *Protein Eng* 8:601-8; Nord et al., 1997, *Nat Bioteehnol* 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins. The phage display library may be screened against any known antigen, using standard phage display screening techniques (e.g., Pasqualini and Ruoslahti, 1996, Nature 380:364-366; Pasqualini, 1999, Quart. J. Nucl. Med. 43:159-162), in order to identify one or more affibodies against the target antigen.

A $^{177}$Lu-labeled affibody specific for HER2/neu has been demonstrated to target HER2-expressing xenografts in vivo (Tolmachev et al., 2007, Cancer Res 67:2773-82). Although renal toxicity due to accumulation of the low molecular weight radiolabeled compound was initially a problem, reversible binding to albumin reduced renal accumulation, enabling radionuclide-based therapy with labeled affibody (Id.).

The feasibility of using radiolabeled affibodies for in vivo tumor imaging has been recently demonstrated (Tolmachev et al., 2011, Bioconjugate Chem 22:894-902). A maleimide-derivatized NOTA was conjugated to the anti-HER2 affibody and radiolabeled with $^{111}$In (Id.). Administration to mice bearing the HER2-expressing DU-145 xenograft, followed by gamma camera imaging, allowed visualization of the xenograft (Id.).

Fynomers, can also bind to target antigens with a similar affinity and specificity to antibodies. Fynomers are based on the human Fyn SH3 domain as a scaffold for assembly of binding molecules. The Fyn SH3 domain is a fully human, 63 amino acid protein that can be produced in bacteria with high yields. Fynomers may be linked together to yield a multispecific binding protein with affinities for two or more different antigen targets. Fynomers are commercially available from COVAGEN AG (Zurich, Switzerland).

The skilled artisan will realize that affibodies or fynomers may be attached to P2PDox and used as targeting molecules in the practice of the claimed methods and compositions.

Nanobodies

Nanobodies are single-domain antibodies of about 12-15 kDa in size (about 110 amino acids in length). Nanobodies can selectively bind to target antigens, like full-size antibodies, and have similar affinities for antigens. However, because of their much smaller size, they may be capable of better penetration into solid tumors. The smaller size also contributes to the stability of the nanobody, which is more resistant to pH and temperature extremes than full size antibodies (Van Der Linden et al., 1999, Biochim Biophys Act 1431:37-46). Single-domain antibodies were originally developed following the discovery that camelids (camels, alpacas, llamas) possess fully functional antibodies without light chains (e.g., Hamsen et al., 2007, Appl Microbiol Biotechnol 77:13-22). The heavy-chain antibodies consist of a single variable domain (Van) and two constant domains ($C_H2$ and $C_H3$). Like antibodies, nanobodies may be developed and used as multivalent and/or bispecific constructs. Humanized forms of nanobodies are in commercial development that are targeted to a variety of target antigens, such as IL-6R, vWF, TNF, RSV, RANKL, IL-17A & F and IgE (e.g., ABLYNX®, Ghent, Belgium), with potential clinical use in cancer, inflammation, infectious disease, Alzheimer's disease, acute coronary syndrome and other disorders (e.g., Saerens et al., 2008, Curr Opin Pharmacol 8:600-8; Muyldermans, 2013, Ann Rev Biochem 82:775-97; Ibanez et al., 2011, J Infect Dis 203:1063-72).

The plasma half-life of nanobodies is shorter than that of full-size antibodies, with elimination primarily by the renal route. Because they lack an Fc region, they do not exhibit complement dependent cytotoxicity.

Nanobodies may be produced by immunization of camels, llamas, alpacas or sharks with target antigen, following by isolation of mRNA, cloning into libraries and screening for antigen binding. Nanobody sequences may be humanized by standard techniques (e.g., Jones et al., 1986, Nature 321: 522, Riechmann et al., 1988, Nature 332: 323, Verhoeyen et al., 1988, Science 239: 1534, Carter et al., 1992, Proc. Nat'l Acad. Sci. USA 89: 4285, Sandhu, 1992, Crit. Rev. Biotech. 12: 437, Singer et al., 1993, J. Immun. 150: 2844). Humanization is relatively straight-forward because of the high homology between camelid and human FR sequences.

In various embodiments, the subject P2PDox conjugates may comprise nanobodies for targeted delivery of conjugated drug to cells, tissues, organs or pathogens. Nanobodies of use are disclosed, for example, in U.S. Pat. Nos. 7,807,162; 7,939,277; 8,188,223; 8,217,140; 8,372,398; 8,557,965; 8,623,361 and 8,629,244, the Examples section of each incorporated herein by reference.)

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074, 405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents, such as P2PDox.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues and one or more haptens for binding, e.g., to a bispecific antibody. Exemplary haptens may include In-DTPA (indium-diethylene triamine pentaacetic acid) or HSG (histamine succinyl glycine). The targetable construct may also comprise one or more chelating moieties, such as DOTA (1,4,7,10-tetraazacyclododecanel,4,7,10-tetraacetic acid), NOTA (1,4,7-triaza-cyclononane-1,4,7-triacetic acid), TETA (p-bromoacetamido-benzyl-tetraethylamine-tetraacetic acid), NETA ([2-(4,7-biscarboxymethyl[1,4,7] triazacyclononan-1-yl-ethyl]-2-carbonylmethyl-amino] acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Preparation of Immunoconjugates

In preferred embodiments, P2PDox or another therapeutic or diagnostic agent may be covalently attached to an antibody or antibody fragment to form an immunoconjugate. In some embodiments, a diagnostic and/or therapeutic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," m MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tomoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2]azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrons were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et, al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Therapeutic and Diagnostic Agents

In certain embodiments, the immunoconjugates or other P2PDox conjugates may be used in combination with one or more therapeutic and/or diagnostic agents. Therapeutic agents may be selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a tyrosine kinase inhibitor, a sphingosine inhibitor, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents, and combinations thereof.

Exemplary drugs may include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), trans-platinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described above.

Toxins may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Immunomodulators may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor and LT.

Chemokines of use include RANTES, MCAF, MIP 1-alpha, MIP 1-Beta and IP-10.

$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$C, $^{51}$Cr, $^{59}$Fe, $^{75}$Se, $^{201}$Tl, $^{225}$Ac, $^{76}$Br, $^{169}$Yb, and the like.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (P1GF) peptides and antibodies, anti-vascular growth factor antibodies (such as anti-VEGF and anti-P1GF), anti-Flk-1 antibodies, anti-Flt-1 antibodies and peptides, anti-Kras antibodies, anti-cMET antibodies, anti-MIF (macrophage migration-inhibitory factor) antibodies laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise an oligonucleotide, such as a siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Formulation and Administration

Suitable routes of administration of the conjugates include, without limitation, oral, parenteral, rectal, transmucosal, intestinal administration, intramedullary, intrathecal, direct intraventricular, intravenous, intravitreal, intracavitary, intraperitoneal, or intratumoral injections. The preferred routes of administration are parenteral, more preferably intravenous. Alternatively, one may administer the compound in a local rather than systemic manner, for example, via injection of the compound directly into a solid or hematological tumor.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the immunoconjugate is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The immunoconjugate can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate from such a matrix depends upon the molecular weight of the immunoconjugate, the amount of immunoconjugate within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered immunoconjugate for humans will vary depending upon such factors as the patient's age, weight, height, sex, general medical condition and previous medical history. It may be desirable to provide the recipient with a dosage of immunoconjugate that is in the range of from about 0.3 mg/kg to 5 mg/kg as a single intravenous infusion, although a lower or higher dosage also may be administered as circumstances dictate. A dosage of 0.3-5 mg/kg for a 70 kg patient, for example, is 21-350 mg, or 12-206 mg/m$^2$ for a 1.7-m patient. The dosage may be repeated as needed, for example, once per week for 2-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 0.3 mg/kg, 0.5 mg/kg, 0.7 mg/kg, 1.0 mg/kg, 1.2 mg/kg, 1.5 mg/kg, 2.0 mg/kg, 2.5 mg/kg, 3.0 mg/kg, 3.5 mg/kg, 4.0 mg/kg, 4.5 mg/kg, and 5.0 mg/kg. More preferred dosages are 0.6 mg/kg for weekly administration and 1.2 mg/kg for less frequent dosing. Any amount in the range of 0.3 to 5 mg/kg may be used. The dosage is preferably administered multiple times, once a week. A minimum dosage schedule of 4 weeks, more preferably 8 weeks, more preferably 16 weeks or longer may be used, with the dose frequency dependent on toxic side-effects and recovery therefrom, mostly related to hematological toxicities. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 2, 4, 6, 8, 10, or 12 times or more.

Alternatively, an immunoconjugate may be administered as one dosage every 2 or 3 weeks, repeated for a total of at least 3 dosages. Or, twice per week for 4-6 weeks. The dosage may be administered once every other week or even less frequently, so the patient can recover from any drug-related toxicities. Alternatively, the dosage schedule may be decreased, namely every 2 or 3 weeks for 2-3 months. The dosing schedule can optionally be repeated at other intervals and dosage may be given through various parenteral routes, with appropriate adjustment of the dose and schedule.

In preferred embodiments, the immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteo sarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudo achondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Autoimmune diseases that may be treated with immunoconjugates may include acute and chronic immune thrombocytopenias, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

In a preferred embodiment, therapeutic conjugates comprising an anti-EGP-1 (anti-TROP-2) antibody such as the hRS7 MAb can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:90); CDR2 (SASYRYT, SEQ ID NO:91); and CDR3 (QQHYITPLT, SEQ ID NO:92) and heavy chain CDR sequences CDR1 (NYGMN, SEQ ID NO:93); CDR2 (WINTYTGEPTYTDDFKG, SEQ ID NO:94) and CDR3 (GGFGSSYWYFDV, SEQ ID NO:95).

In another preferred embodiment, therapeutic conjugates comprising an anti-CEACAM5 antibody (e.g., hMN-14, labretuzumab) and/or an anti-CEACAM6 antibody (e.g., hMN-3 or hMN-15) may be used to treat any of a variety of cancers that express CEACAM5 and/or CEACAM6, as disclosed in U.S. Pat. Nos. 7,541,440; 7,951,369; 5,874,540; 6,676,924 and 8,267,865, the Examples section of each incorporated herein by reference. Solid tumors that may be treated using anti-CEACAM5, anti-CEACAM6, or a combination of the two include but are not limited to breast, lung, pancreatic, esophageal, medullary thyroid, ovarian, colon, rectum, urinary bladder, mouth and stomach cancers. A majority of carcinomas, including gastrointestinal, respiratory, genitourinary and breast cancers express CEACAM5 and may be treated with the subject immunoconjugates. An hMN-14 antibody is a humanized antibody that comprises light chain variable region CDR sequences CDR1 (KASQDVGTSVA; SEQ ID NO:96), CDR2 (WTSTRHT; SEQ ID NO:97), and CDR3 (QQYSLYRS; SEQ ID NO:98), and the heavy chain variable region CDR sequences CDR1 (TYWMS; SEQ ID NO:99), CDR2 (EIHPDSSTINYAPSLKD; SEQ ID NO:100) and CDR3 (LYFGFPWFAY; SEQ ID NO:101). An hMN-3 antibody is a humanized antibody that comprises light chain variable region CDR sequences CDR1 (RSSQSIVHSNGNTYLE, SEQ ID NO:102), CDR2 (KVSNRFS, SEQ ID NO:103) and CDR3 (FQGSHVPPT, SEQ ID NO:104) and the heavy chain CDR sequences CDR1 (NYGMN, SEQ ID NO:105), CDR2 (WINTYTGEPTYTDDFKG, SEQ ID NO:106) and CDR3 (KGWMDFNSSLDY, SEQ ID NO:107). An hMN-15 antibody is a humanized antibody that comprises light chain variable region CDR sequences SASSRVSYIH (SEQ ID NO:108); GTSTLAS (SEQ ID NO:109); and QQWSYNPPT (SEQ ID NO:110); and heavy chain variable region CDR sequences DYYMS (SEQ ID NO:111); FIANKANGHTTDYSPSVKG (SEQ ID NO:112); and DMGIRWNFDV (SEQ ID NO:113).

In another preferred embodiment, therapeutic conjugates comprising an anti-CD74 antibody (e.g., hLL1, milatuzumab, disclosed in U.S. Pat. Nos. 7,074,403; 7,312,318; 7,772,373; 7,919,087 and 7,931,903, the Examples section of each incorporated herein by reference) may be used to treat any of a variety of cancers that express CD74, including but not limited to renal, lung, intestinal, stomach, breast, prostate or ovarian cancer, as well as several hematological cancers, such as multiple myeloma, chronic lymphocytic leukemia, acute lymphoblastic leukemia, non-Hodgkin lymphoma, and Hodgkin lymphoma. An hLL1 antibody is a humanized antibody comprising the light chain CDR sequences CDR1 (RSSQSLVHRNGNTYLH; SEQ ID NO:114), CDR2 (TVSNRFS; SEQ ID NO:115), and CDR3 (SQSSHVPPT; SEQ ID NO:116) and the heavy chain variable region CDR sequences CDR1 (NYGVN; SEQ ID NO:117), CDR2 (WINPNTGEPTFDDDFKG; SEQ ID NO:118), and CDR3 (SRGKNEAWFAY; SEQ ID NO:119).

In another preferred embodiment, therapeutic conjugates comprising an anti-CD22 antibody (e.g., hLL2, epratuzumab, disclosed in U.S. Pat. Nos. 5,789,554; 6,183,744; 6,187,287; 6,306,393; 7,074,403 and 7,641,901, the Examples section of each incorporated herein by reference, or the chimeric or humanized RFB4 antibody) may be used to treat any of a variety of cancers that express CD22, including but not limited to indolent forms of B-cell lymphomas, aggressive forms of B-cell lymphomas, chronic lymphatic leukemias, acute lymphatic leukemias, non-Hodgkin's lymphoma, Hodgkin's lymphoma, Burkitt lymphoma, follicular lymphoma or diffuse B-cell lymphoma. An hLL2 antibody is a humanized antibody comprising light chain CDR sequences CDR1 (KSSQSVLYSANHKYLA, SEQ ID NO:120), CDR2 (WASTRES, SEQ ID NO:121), and CDR3 (HQYLSSWTF, SEQ ID NO:122) and the heavy chain CDR sequences CDR1 (SYWLH, SEQ ID NO:123), CDR2 (YINPRNDYTEYNQNFKD, SEQ ID NO:124), and CDR3 (RDITTFY, SEQ ID NO:125).

In a preferred embodiment, therapeutic conjugates comprising anti-CSAp antibodies, such as the hMu-9 MAb, can be used to treat colorectal, as well as pancreatic and ovarian cancers as disclosed in U.S. Pat. Nos. 6,962,702; 7,387,772; 7,414,121; 7,553,953; 7,641,891 and 7,670,804, the Examples section of each incorporated herein by reference. In addition, therapeutic conjugates comprising the hPAM4 MAb can be used to treat pancreatic cancer or other solid tumors, as disclosed in U.S. Pat. Nos. 7,238,786 and 7,282,567, the Examples section of each incorporated herein by reference. An hMu-9 antibody is a humanized antibody comprising light chain CDR sequences CDR1 (RSSQSIVHSNGNTYLE, SEQ ID NO:126), CDR2 (KVSNRFS, SEQ ID NO:127), and CDR3 (FQGSRVPYT, SEQ ID NO:128), and heavy chain variable CDR sequences CDR1 (EYVIT, SEQ ID NO:129), CDR2 (EIYPGSGSTSYNEKFK, SEQ ID NO:130), and CDR3 (EDL, SEQ ID NO:131).

In another preferred embodiment, therapeutic conjugates comprising an anti-MUC5ac antibody such as the hPAM4 MAb can be used to treat cancers, such as pancreatic, stomach, colon or lung cancer, as disclosed in U.S. Pat. Nos. 7,238,786; 7,282,567; 8,491,896 and 8,574,854; the Examples section of which is incorporated herein by reference. An hPAM4 antibody is a humanized antibody comprising light chain variable region CDR sequences CDR1 (SASSSVSSSYLY, SEQ ID NO:132); CDR2 (STSNLAS, SEQ. ID NO:133); and CDR3 (HQWNRYPYT, SEQ ID NO:134); and heavy chain CDR sequences CDR1 (SYVLH, SEQ ID NO:135); CDR2 (YINPYNDGTQYNEKFKG, SEQ ID NO:136) and CDR3 (GFGGSYGFAY, SEQ ID NO:137).

In another preferred embodiment, therapeutic conjugates comprising an anti-AFP MAb, such as IMMU-31, can be used to treat hepatocellular carcinoma, germ cell tumors, and other AFP-producing tumors using humanized, chimeric and human antibody forms, as disclosed in U.S. Pat. No. 7,300,655, the Examples section of which is incorporated herein by reference. An IMMU-31 antibody is a humanized antibody comprising the heavy chain CDR sequences CDR1 (SYVIH, SEQ ID NO:138), CDR2 (YIHPYNGGTKYNEKFKG, SEQ ID NO:139) and CDR3 (SGGGDPFAY, SEQ ID NO:140) and the light chain CDR1 (KASQDINKYIG, SEQ ID NO:141), CDR2 (YTSALLP, SEQ ID NO:142) and CDR3 (LQYDDLWT, SEQ ID NO:143).

In another preferred embodiment, therapeutic conjugates comprising an anti-HLA-DR MAb, such as hL243, can be used to treat lymphoma, leukemia, cancers of the skin, esophagus, stomach, colon, rectum, pancreas, lung, breast, ovary, bladder, endometrium, cervix, testes, kidney, liver, melanoma or other HLA-DR-producing tumors, as disclosed in U.S. Pat. No. 7,612,180, the Examples section of which is incorporated herein by reference. An hL243 antibody is a humanized antibody comprising the heavy chain CDR sequences CDR1 (NYGMN, SEQ ID NO:144), CDR2 (WIN-TYTREPTYADDFKG, SEQ ID NO:145), and CDR3 (DI-TAVVPTGFDY, SEQ ID NO:146) and light chain CDR sequences CDR1 (RASENIYSNLA, SEQ ID NO:147), CDR2 (AASNLAD, SEQ ID NO:148), and CDR3 (QHFWT-TPWA, SEQ ID NO:149).

In another preferred embodiment, therapeutic conjugates comprising an anti-CD20 MAb, such as veltuzumab (hA20), 1F5, obinutuzumab (GA101), or rituximab, can be used to treat lymphoma, leukemia, immune thrombocytopenic purpura, systemic lupus erythematosus, Sjögren's syndrome, Evans syndrome, arthritis, arteritis, pemphigus vulgaris, renal graft rejection, cardiac graft rejection, rheumatoid arthritis, Burkitt lymphoma, non-Hodgkin's lymphoma, follicular lymphoma, small lymphocytic lymphoma, diffuse B-cell lymphoma, marginal zone lymphoma, chronic lymphocytic leukemia, acute lymphocytic leukemia, Type I diabetes mellitus, GVHD, multiple sclerosis or multiple myeloma, as disclosed in U.S. Pat. Nos. 7,435,803 or 8,287,864, the Examples section of each incorporated herein by reference. An hA20 (veltuzumab) antibody is a humanized antibody comprising the light chain CDR sequences CDRL1 (RASSSVSYIH, SEQ ID NO:150), CDRL2 (ATSNLAS, SEQ ID NO:151) and CDRL3 (QQWTSNPPT, SEQ ID NO:152) and heavy chain CDR sequences CDRH1 (SYNMH, SEQ ID NO:153), CDRH2 (AIYPGNGDTSYN-QKFKG, SEQ ID NO:154) and CDRH3 (STYYGGDWY-FDV, SEQ ID NO:155).

In another preferred embodiment, therapeutic conjugates comprising an anti-CD19 MAb, such as hA19, can be used to treat B-cell related lymphomas and leukemias, such as non-Hodgkin's lymphoma, chronic lymphocytic leukemia or acute lymphoblastic leukemia. Other disease states that may be treated include autoimmune diseases, such as acute or chronic immune thrombocytopenia, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis, as disclosed in U.S. Pat. Nos. 7,109,304, 7,462,352, 7,902,338, 8,147,831 and 8,337,840, the Examples section of each incorporated herein by reference. An hA19 antibody is a humanized antibody comprising the light chain CDR sequences CDR1 KASQSVDYDGDSYLN (SEQ ID NO: 156); CDR2 DASNLVS (SEQ ID NO: 157); and CDR3 QQSTEDPWT (SEQ ID NO: 158) and the heavy chain CDR sequences CDR1 SYWMN (SEQ ID NO: 159); CDR2 QIWPGDGDT-NYNGKFKG (SEQ ID NO: 160) and CDR3 RETTTVGRYYYAMDY (SEQ ID NO: 161).

Kits

Various embodiments may concern kits containing components suitable for treating diseased tissue in a patient. Exemplary kits may contain at least one conjugated antibody or other targeting moiety as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

Production and Use of Pro-2-Pyrrolinodoxorubicin (P2PDox)

Synthesis

Structures of intermediates in the synthetic pathway of P2PDox, as well as a maleimide derivative of P2PDox suitable for conjugation to antibodies or other proteins or sulthydryl-containing peptides, are shown in FIG. 1A-D. A general scheme for producing an exemplary P2PDox is shown in Scheme 1 below. We have performed 1-g scale reactions to generate >1 g of 4,4-diacetoxybutyraldehyde in an yield of ~40%. To avoid using sodium cyanoborohydride that can potentially contaminate products with cyanide, the reducing agent was changed to sodium triacetoxyborohydride in reductive alkylation. On an exploratory scale, >80% conversion of doxorubicin to P2PDox was recorded. This was increased to 2-g scale to generate >1 g of P2PDox. (Scheme 1). The 4,4-diacetoxybutyraldehyde was prepared by a modification of the reported method (Nagy et al., 1998, Proc Natl Acad Sci USA 95:1794-9), which was necessary to avoid a hazardous ozonolysis step. Diacetoxylation of commercially available 4-pentene-1-al with acetic anhydride and indium chloride catalysis, followed by oxidative cleavage of olefin by ruthenium chloride and sodium periodate combination (Yang & Zhang, 2001, 66:4814-8) furnished the 4,4-diacetoxybutyraldehyde, which was reductively coupled to doxorubicin to obtain P2PDox. The following steps were involved: (i) To a mixture of acetic anhydride (7.45 mL) and indium chloride (0.56 g) in dichloromethane (20 mL) was added 5.05 g of 4-penten-1-al. After 10 to 30 mM, the reaction mixture was treated with 25% aqueous sodium acetate (20 mL), and the organic layer was washed with brine and dried. Solvent removal gave 15.3 g of the liquid product, which was taken to the next step; (ii) 3.5 mM ruthenium chloride stock solution in water (69.4 mL) was added to the solution of the step (i) product in dichloromethane in 6:1 acetonitrile-water (350 mL). Sodium periodate (29.7 g) was added in portions. After completion of reaction, as judged by TLC analysis, the reaction mixture was treated with 30 mL of saturated sodium thiosulfate, filtered through a pad of celite, and acetonitrile was evaporated off. The remaining aqueous layer was extracted with ethyl acetate, washed with 25% sodium acetate, water, and brine, and dried. The crude material was purified by chromatography on silica gel using ethyl acetate-hexane mixture for elution. The pure product was used for reductive alkylation of doxorubicin in the next step; (iii) 1.5 grams of doxorubicin hydrochloride was dissolved in 1,1,1,3,3,3,-hexafluoroisopropanol (195 mL) and diisopropylethylamine (2.7 mL), and reacted with 3.4 g (7-fold molar excess) of the aldehyde from step (ii) and 0.66 g of sodium triacetoxyborohydride. The reaction was complete in 10 min, and the product was purified on silica gel using methylene chloride-isopropanol mixtures for elution, resulting in 0.96 g of pure product. Electrospray mass spectrum showed the mass at m/z 716.2570 (M+H) consistent with the structure of the product. The structure was also confirmed by proton and C-13 NMR spectra. (iv) P2PDox from step iii was converted to MCC hydrazone as follows: To 0.6 g of P2PDox dissolved in 75 mL of anhydrous methanol, and treated with 0.34 g of SMCC hydrazide, calculated to be 1.8-fold excess based on the spectrophotometric quantification of the amount of P2PDox used. The percent conversion was judged to be 88% by HPLC. LC-MS analysis the showed the product peak at ink of 949.3734 (M+H), consistent with the calculated mass (m/z) of 949.3713 (M+H). The material, after solvent removal, was used as such for conjugation since underivatized starting material did not conjugate and was removed during conjugate purification process.

Small-Scale Conjugate Preparation

Conjugate preparation followed a general methodology of mildly reducing interchain disulfides of IgG with TCEP in PBS, followed by coupling to a 10-fold excess of activated P2PDox. The conjugates were purified on centrifuged size exclusion chromatography (SEC) on SEPHADEX® equilibrated in 25 mM 3-(N-morpholino)propanesulfonic acid (MOPS), pH 6.8, followed by passage over a hydrophobic column. The products were formulated with trehalose and polysorbate 80, and lyophilized. The conjugated product, with a substitution in the range of 4-7 drug/IgG, eluted as a single peak by size-exclusion HPLC, and contained typically <1% of unconjugated free drug by reversed-phase HPLC.

Scaled-Up Conjugate Preparation

Conjugate of humanized anti-TROP-2 antibody, hRS7, was prepared, on 5-g and 10-g scale, by TCEP reduction of an antibody, followed by in situ conjugation using a 12-fold excess of activated P2PDox, with DMSO as co-solvent (5% v/v). The product was purified by tangential flow filtration using 25 mM MOPS buffer, pH 6.8, with 20-diafiltration volumes for purification. The product was formulated with 25 mM trehalose and 0.01% TWEEN® 80, aliquotted in 20-mg or 100-mg lots, and lyophilized.

Representative Conjugates

|   | Conjugate | Lot | % Protein recover | P2PDox/ IgG | HPLC Aggr. | Free drug |
| --- | --- | --- | --- | --- | --- | --- |
| 1 | hIMMU-31-P2PDox | II22-138 | 75.0% | 7.39 | 1.9% | 0.26% |
| 2 | hA20-P2PDox | II22-135 | 85.7% | 6.79 | <2% | <0.1% |
| 3 | hLL1-P2PDox | II22-145 | 88.6% | 7.10 | 2.8% | 0.2% |
| 4 | hRS7-P2PDox | II22-142 | 80.1% | 7.17 | 1.8% | 0.12% |
| 5 | hMN15-P2PDox | II22-180 | 74.9% | 6.87 | 1.1% | 0.46% |
| 6 | hMN-14-P2PDox | II22-183 | 80.2% | 6.78 | 2.1% | 0.53% |

Conjugates have also been prepared for hPAM4-P2PDox, hLL2-P2PDox and RFB4-P2PDox, with similar protein recovery and purity (not shown).

Example 2

In Vitro Preclinical Studies

In Vitro Cell-Binding Studies—

Retention of antibody binding was confirmed by cell binding assays comparing binding of the conjugate to unconjugated antibody (Chan, 2008, Acc Chem Res 41:98-107). The potency of the conjugate was tested in a 4-day MTS assay using appropriate target cells. The hRS7-P2PDox conjugate exhibited $IC_{50}$ values of 0.35-1.09 nM in gastric (NCI-N87), pancreatic (Capan-1), and breast (MDA-MB-468) human cancer cell lines, with free drug exhibiting 0.02-0.07 nM potency in the same cell lines.

Serum Stability—

Serum stability of prototypical P2PDox conjugate, hRS7-P2PDox, was determined by incubating in human serum at a concentration of 0.2 mg/ml at 37° C. The incubate was analyzed by HPLC using butyl hydrophobic interaction chromatography (HIC) column in which there was good retention time separation between the peak due to free drug and that due to conjugate or higher molecular weight species. This analysis showed that there was no release of free drug from the conjugate, suggesting high serum stability of the conjugate. When the same experiment was repeated with hRS7-doxoru-

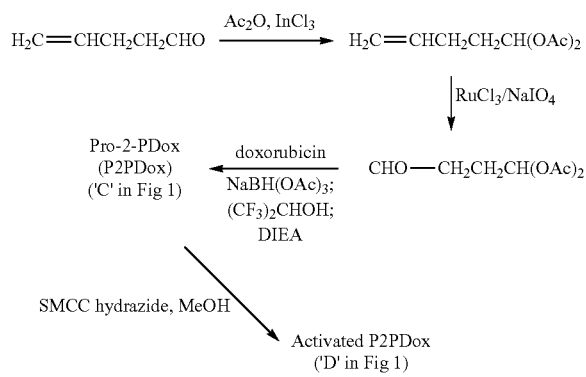

Scheme-1 bicin conjugate, containing the same cleavable linker as hRS7-P2PDox, and where the free drug was independently verified to be released with a half-life of 96 h, clear formation of free drug peak, namely doxorubicin peak, was seen on HIC HPLC.

Surprisingly, it was determined that the P2PDox conjugate was held tightly to the antibody because it cross-linked the peptide chains of the antibody together. The cross-linking stabilizes the attachment of the drug to the antibody so that the drug is only released intracellularly after the antibody is metabolized. The cross-linking assists in minimizing toxicity, for example cardiotoxicity, that would result from release of free drug in circulation. Previous use of 2-PDox peptide conjugates failed because the drug cross-linked the peptide to other proteins or peptides in vivo. With the present conjugates, the P2PDox is attached to interchain disulfide thiol groups while in the prodrug form. The prodrug protection is rapidly removed in vivo soon after injection and the resulting 2-PDox portion of the conjugate cross-links the peptide chains of the antibody, forming intramolecular cross-linking within the antibody molecule. This both stabilizes the ADC and prevents cross-linking to other molecules in circulation.

Example 3

In Vivo Preclinical Studies

General—

Tumor size was determined by caliper measurements of length (L) and width (W) with tumor volume calculated as $(L \times W^2)/2$. Tumors were measured and mice weighed twice a week. Mice were euthanized if their tumors reached >1 cm$^3$ in size, lost greater than 15% of their starting body weight, or otherwise became moribund. Statistical analysis for the tumor growth data was based on area under the curve (AUC) and survival time. Profiles of individual tumor growth were obtained through linear curve modeling. Anfitest was employed to determine equality of variance between groups prior to statistical analysis of growth curves. A two-tailed t-test was used to assess statistical significance between all the various treatment groups and non-specific controls. For the saline control analysis a one-tailed t-test was used to assess significance. Survival studies were analyzed using Kaplan-Meier plots (log-rank analysis), using the Prism GraphPad Software (v4.03) software package (Advanced Graphics Software, Inc.; Encinitas, Calif.). All doses in preclinical experiments are expressed in antibody amounts. In terms of drug, 100 µg of antibody (5 mg/kg) in a 20-g mouse, for example, carries 1.4 µg-2.8 (0.14-0.17 mg/kg) of P2PDox equivalent dose when using an ADC with 3-6 drugs/IgG.

Figure 3A:
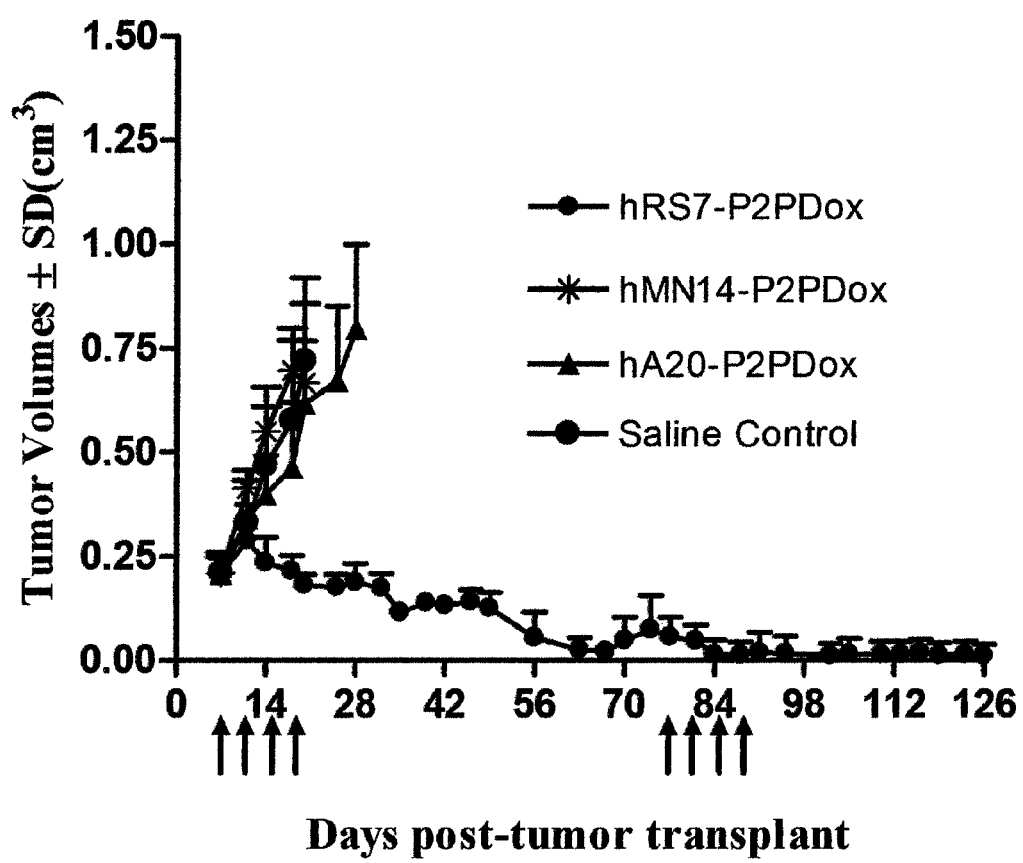
FIG. 3A. Therapy in nude mice bearing s.c. human tumor xenografts using 2.25 mg/kg protein dose (0.064 mg/kg of drug dose) of MAb-P2PDox conjugates twice weekly×2 weeks in nude mice (n=7) with NCI-N87 human gastric carcinoma xenografts.
Figure 3B:
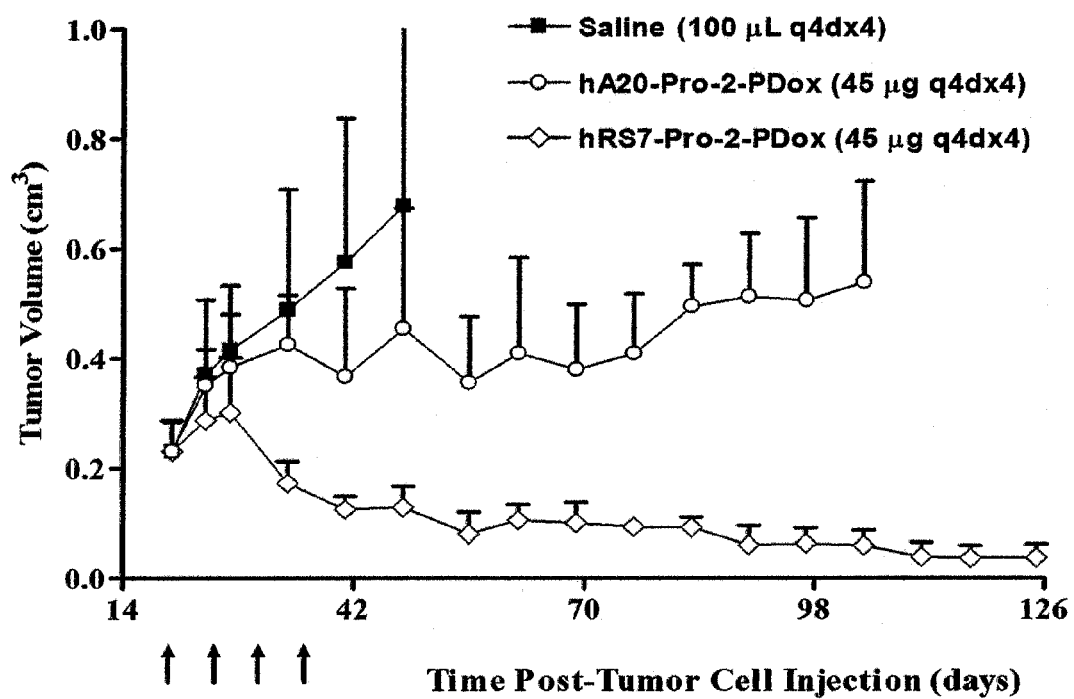
FIG. 3B. Therapy in nude mice bearing s.c. human tumor xenografts using 2.25 mg/kg protein dose (0.064 mg/kg of drug dose) of MAb-P2PDox conjugates twice weekly×2 weeks in nude mice (n=7) with MDA-MB-468 human breast carcinoma xenografts.
Figure 3C:
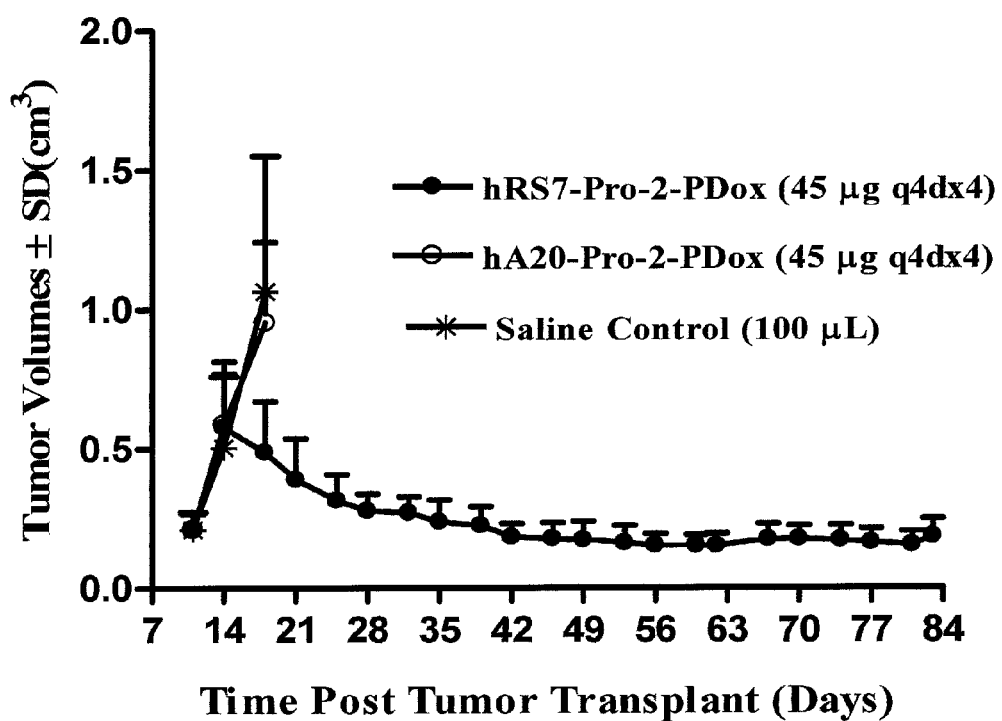
FIG. 3C. Therapy in nude mice bearing s.c. human tumor xenografts using 2.25 mg/kg protein dose (0.064 mg/kg of drug dose) of MAb-P2PDox conjugates twice weekly×2 weeks in nude mice (n=7) with BxPC3 human pancreatic carcinoma xenografts.

A single i.v. dose of ≥300 µg [~10 µg of P2PDox] of the conjugate was lethal, but 4 doses of 45 µg given in 2 weeks were tolerated by all animals. Using this dosing regimen, we examined the therapeutic effect of hRS7-P2PDox in 2 human tumor xenograft models, Capan-1 (pancreatic cancer) and NCI-N87 (gastric cancer). Therapy began 7 days after tumor transplantation in nude mice. In the established, 7-day-old, Capan-1 model, 100% of established tumors quickly regressed, with no evidence of re-growth (FIG. 2). This result was reproduced in a repeat experiment (not shown). Similar findings were made in the established NCI-N87 model (FIG. 3), where a 2$^{nd}$ course of therapy, administered after day 70, was safely tolerated and led to further regressions of residual tumor (FIG. 3). The internalizing hRS7-SN-38 conjugate, targeting Trop-2, provided better therapeutic responses than a conjugate of a poorly internalizing anti-CEACAM5 antibody, hMN-14 (FIG. 2, FIG. 3). A non-targeted anti-CD20 ADC, hA20-P2PDox, was ineffective, indicating selective therapeutic efficacy (FIG. 2, FIG. 3). Data from a breast cancer xenograft (MDA-MB-468) and a second pancreatic cancer xenograft (FIG. 3A and FIG. 3B, respectively) reiterate the same trend of the conjugate's specific and significant antitumor effects.

PK and Toxicity of hRS7-P2PDox with Substitutions of 6.8 or 3.7 Drug/IgG—

Antibody-drug conjugates (ADCs) carrying as much as 8 ultratoxic drugs/MAb are known to clear faster than unmodified MAb and to increase off-target toxicity, a finding that has led to the current trends to use drug substitutions of ≤4 (Hamblett et al., 2004, Clin Cancer Res 10:7063-70). Conjugates were prepared and evaluated with mean drug/MAb substitution ratios (MSRs) of ~6:1 and ~3:1. Groups of normal mice (n=5) were administered, i.v., single doses of unmodified hRS7 or hRS7-P2PDox with drug substitution of 6.8 or 3.7 (same protein dose), and serum samples were collected at 30 min, 4 h, 24 h, 72 h, and 168 h post-injection. These were analyzed by ELISA for antibody concentration. There were no significant differences in serum concentrations at various times, indicating that these cleared similarly. The PK parameters (Cmax, AUC, etc.) were similar. Conjugates with either higher or lower drug substitution had similar tolerability in nude mice, when the administered at the same dose of conjugated drug.

Therapeutic Efficacy at Minimum Effective Dose (MED)—

Anti-TROP-2 antibody conjugate, hRS7-P2PDox, was evaluated in nude mice bearing NCI-N87 human gastric cancer xenografts by administering a single bolus protein dose of 9 mg/kg, 6.75 mg/kg, 4.5 mg/kg, 2.25 mg/kg, or 1 mg/kg. The therapy was started when the mean tumor volume (mTV) was 0.256 cm$^3$. On day 21, mTV in the saline control group (non-treatment group) was 0.801±0.181 cm$^3$ which was significantly larger than that in mice treated with 9, 6.75, 4.5, or 2.25 mg/kg dose with mTV of 0.211±0.042 cm$^3$, 0.239±0.0.054 cm$^3$ 0.264±0.087 cm$^3$, and 0.567±0.179 cm$^3$, respectively (P<0.0047, one tailed t-test). From these, the minimum effective dose was judged to be 2.25 mg/kg, while 9 mg/kg represented MTD.

Example 4

MTD of Antibody-P2PDox

An MTD study comparing 2-PDox and P2PDox conjugates of prototype antibody, hLL1, in mice demonstrated that the P2PDox conjugate was much more potent (not shown). The MTD of a single i.v. injection was between 100 and 300 µg. The MTD of multiple injections, at a schedule of every four days for a total of four injections (q4dx4) was then determined, using protein doses between 25 µg to 150 µg per injection. At these doses, a cumulative dose of between 100 and 600 µg was given to the animals. Table 6 below summarizes the various groups.

TABLE 6

Dosage and Schedule for MTD of antibody-P2PDox
12 Female Athymic Nude Mice

| Group | N | Treatment | Total Amount |
|---|---|---|---|
| 1 | 3 | 25 µg i.v. q4dx4 | 100 µg |
| 2 | 3 | 50 µg i.v. q4dx4 | 200 µg |
| 3 | 3 | 100 µg i.v. q4dx4 | 400 µg |
| 4 | 3 | 150 µg i.v. q4dx4 | 600 µg |

Graphs showing weight loss are shown in FIG. 4A-4D. Only those mice treated with 25 µg P2PDox-ADC continue to show no signs of toxicity. This is a cumulative dose of 100 µg which was also the dose tolerated when administered as a single injection (not shown). Therefore, the MTD for multiple injections of a P2PDox-ADC in mice is 25 µg q4dx4 from this experiment. A careful analysis of data and repetition of the experiment established the MTD for fractionated dosing to be 45 µg of protein dose of the conjugate, administered every 4 days for 2 weeks (45 µg, q4dx4 schedule).

Example 5

Alternative Structures of P2PDox for ADC Conjugation

Figure 5:
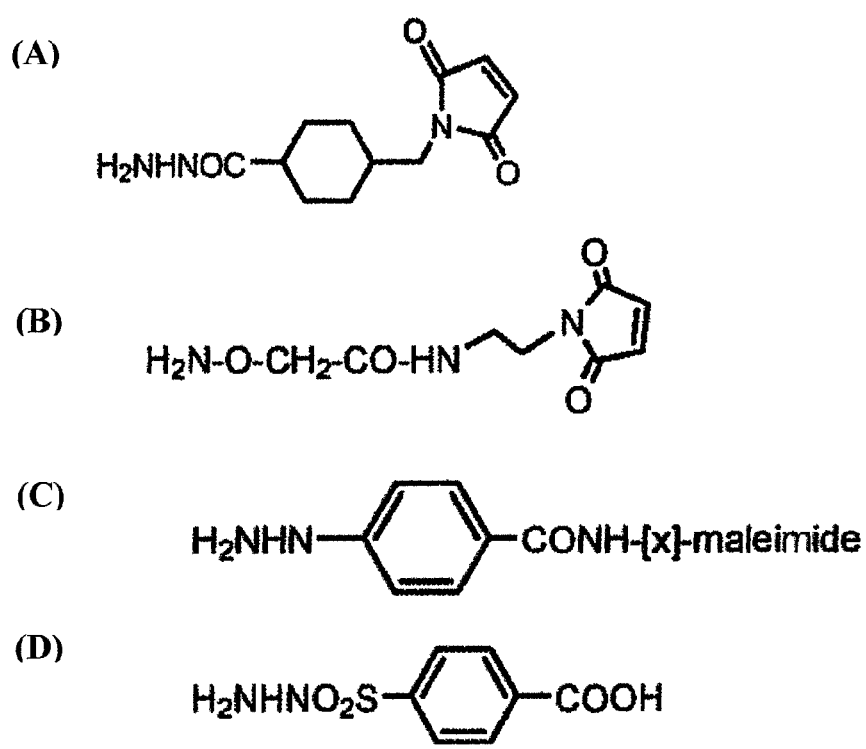
FIG. 5A. Activated form of P2PDox, prepared using a hydrazide linker.
FIG. 5B. Activated form of P2PDox, prepared using an aminoxy linker.
FIG. 5C. Activated form of P2PDox, prepared using a phenylhydrazine linker.
FIG. 5D. Activated form of P2PDox, prepared using a 4-(hydrazinosulfonyl)benzoic acid linker.

Alternative cross-linkers, of use for conjugation of P2PDox to antibodies, antibody fragments, targetable constructs or other targeting molecules, are shown in FIG. 5A-D. FIG. 5A shows an SMCC hydrazide cross-linker, which forms an acylhydrazone with P2PDox. FIG. 5B shows an aminoxy cross-linker, which forms an oxime with P2PDox. FIG. 5C shows a phenylhydrazine cross-linker, which forms a phenylhydrazone with P2PDox. The SMCC hydrazide, aminoxy and phenylhydrazone cross-linkers are used to produce a maleimide derivatized P2PDox, which can be attached to any free sulfhydryl group. FIG. 5D shows an 4-(hydrazinosulfonyl)benzoic acid cross-linker. The linkers have different intrinsic rates of cleavage. Acylhydrazone is cleaved relatively rapidly, while the oxime and phenylhydrazone derivatives are more stable (Mueller et al., 1990, Bioconj Chem 1:325-30).

The SMCC hydrazide and aminoxy cross-linkers were coupled to the C-13 ketone group of P2PDox and the conjugates of a number of antibodies were prepared. In vitro data showed that the acylhydrazone derivatived conjugates showed good activity, while the activity of oxime derivatized ADCs was attenuated. Derivatives with SMCC hydrazide, aminoxy, phenylhydrazide and 4-(hydrazinosulfonyl)benzoic acid cross-linkers were also prepared and attached to peptide targeting moieties.

Example 6

Intracellular Cleavage of 2-PDox from ADCs

Figure 6:
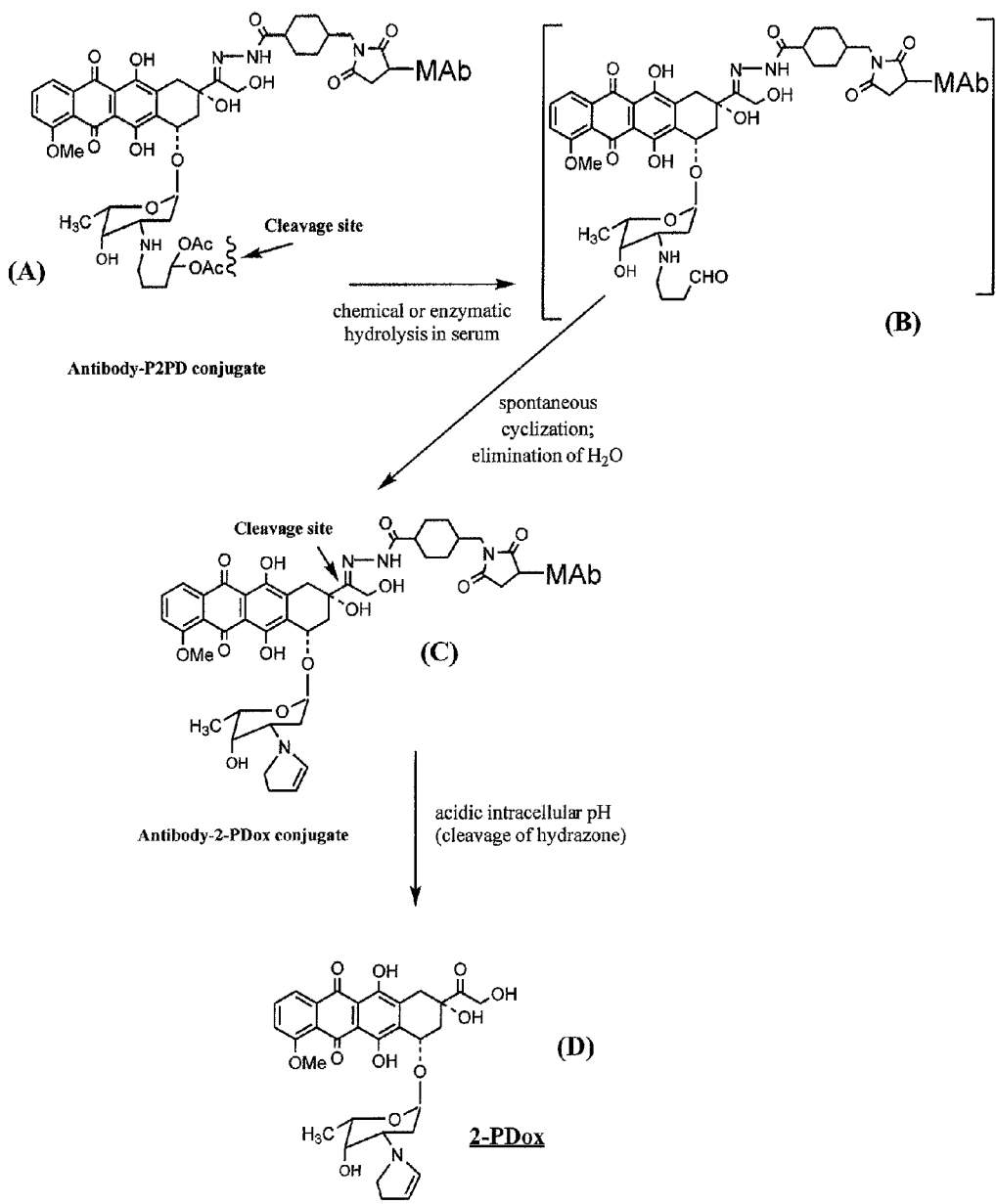
FIG. 6A. Intracellular cleavage of P2PDox ADCs. Hydrazide derivatized P2PDox ADC.
FIG. 6B. Intracellular cleavage of P2PDox ADCs. Esterase activity or basic pH produces an unstable intermediate conjugate.
FIG. 6C. Intracellular cleavage of P2PDox ADCs. Spontaneous cyclization results in 2-PDox conjugate.
FIG. 6D. Intracellular cleavage of P2PDox ADCs. Acidic cleavage in lysosomes yields free 2-PDox.

A proposed scheme for intracellular cleavage of 2-PDox from P2PDox ADC conjugates is shown in FIG. 6A-D. The acetate groups in P2PDox ADC (FIG. 6A) are removed by chemical or enzymatic process in serum to generate an unstable intermediate (FIG. 6B), which undergoes spontaneous cyclization with elimination of water to produce the highly cytotoxic conjugate of 2-PDox (FIG. 6C). After internalization and intracellular transport to lysosomes, the hydrazone moiety of the conjugate is cleaved at the indicated site by acidic conditions inside the lysosome to generate free 2-PDox (FIG. 6D).

Example 7

Peptide Conjugated P2PDox

Figure 7:
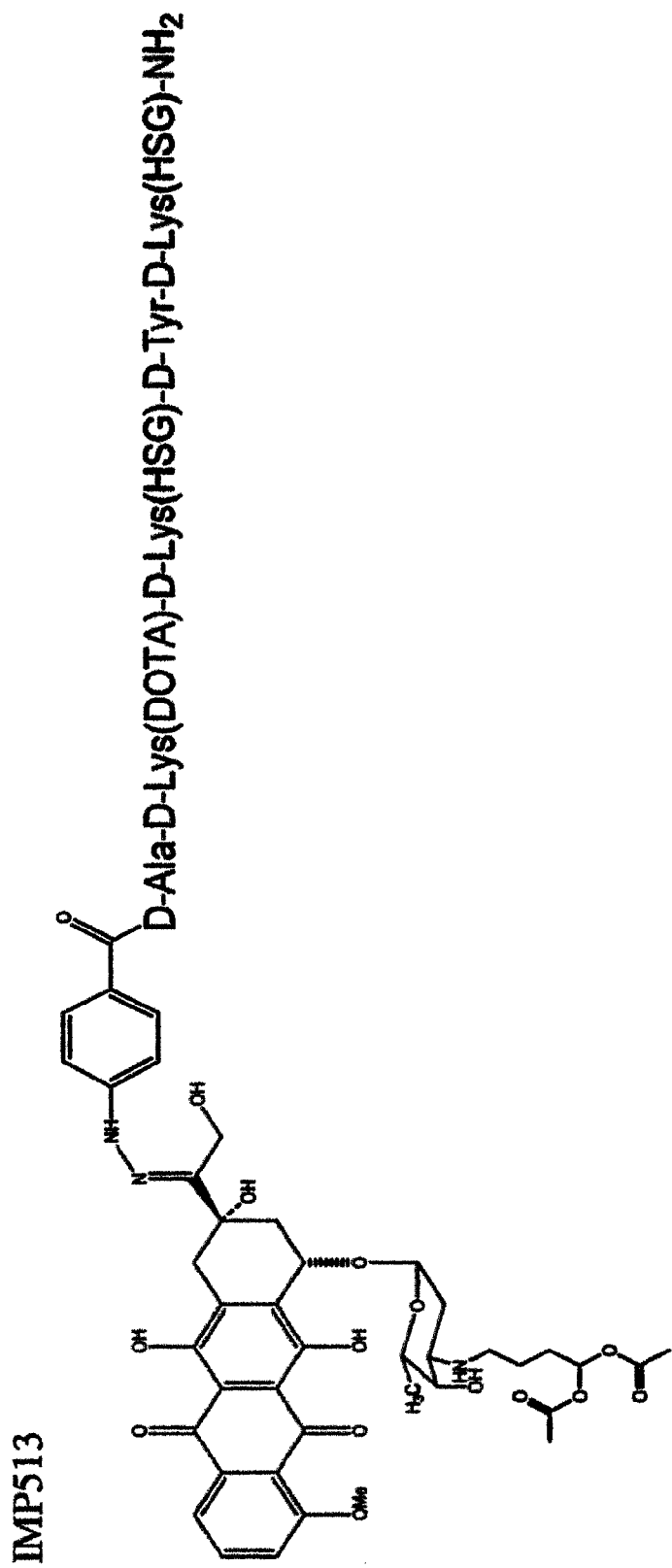
FIG. 7. Structure of peptide conjugated P2PDox, IMP513.
Figure 8:
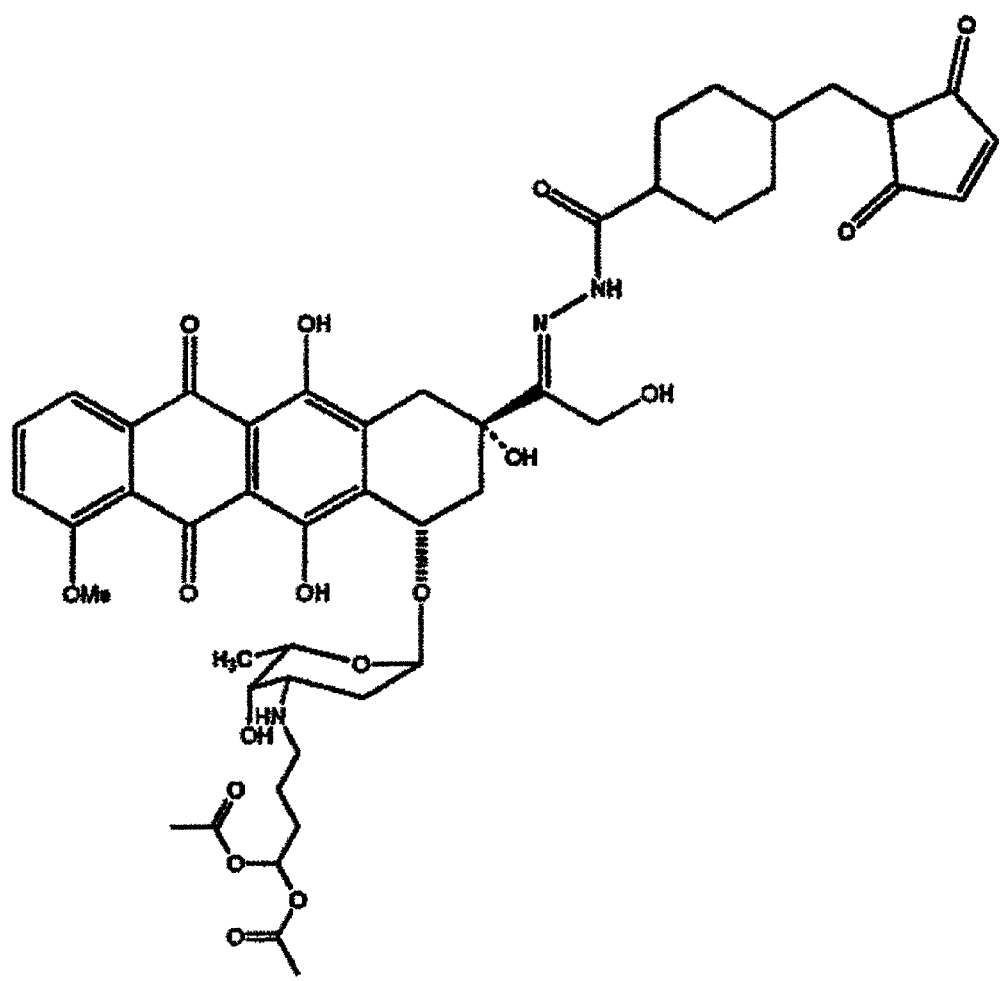
FIG. 8. Structure of IMP402.
Figure 9:
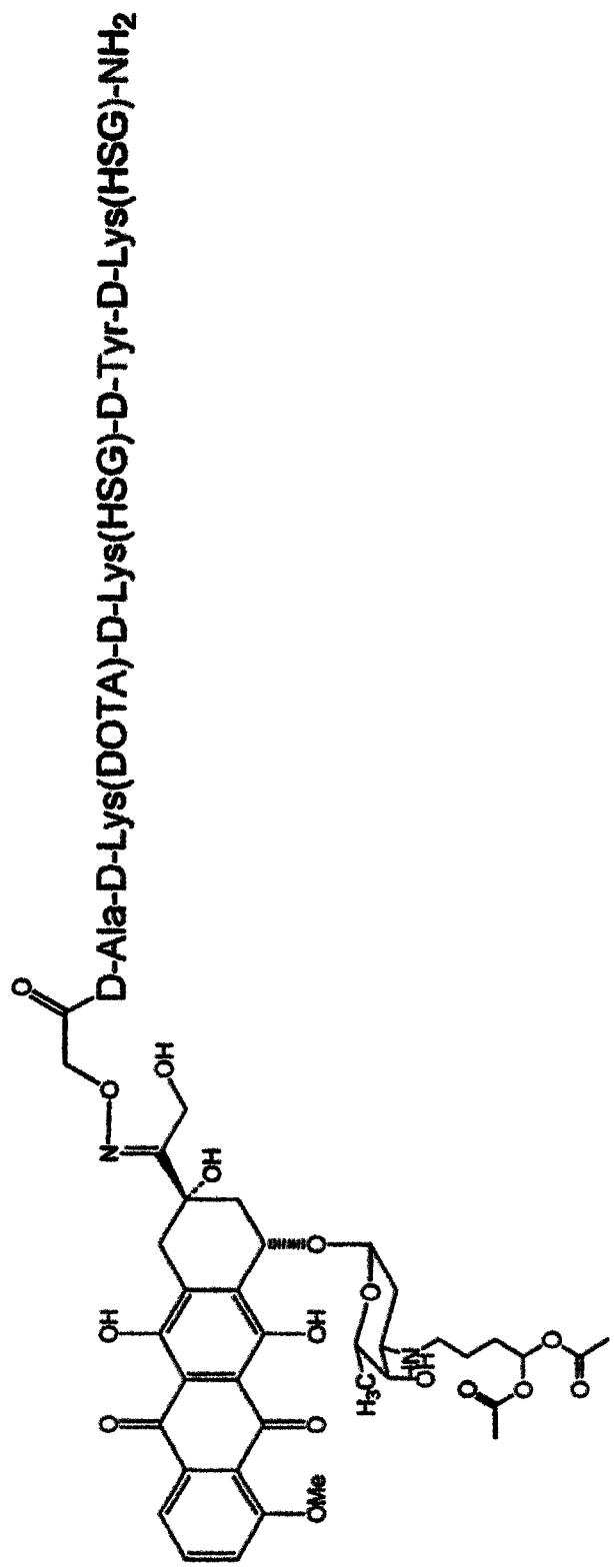
FIG. 9. Structure of IMP514.
Figure 10:
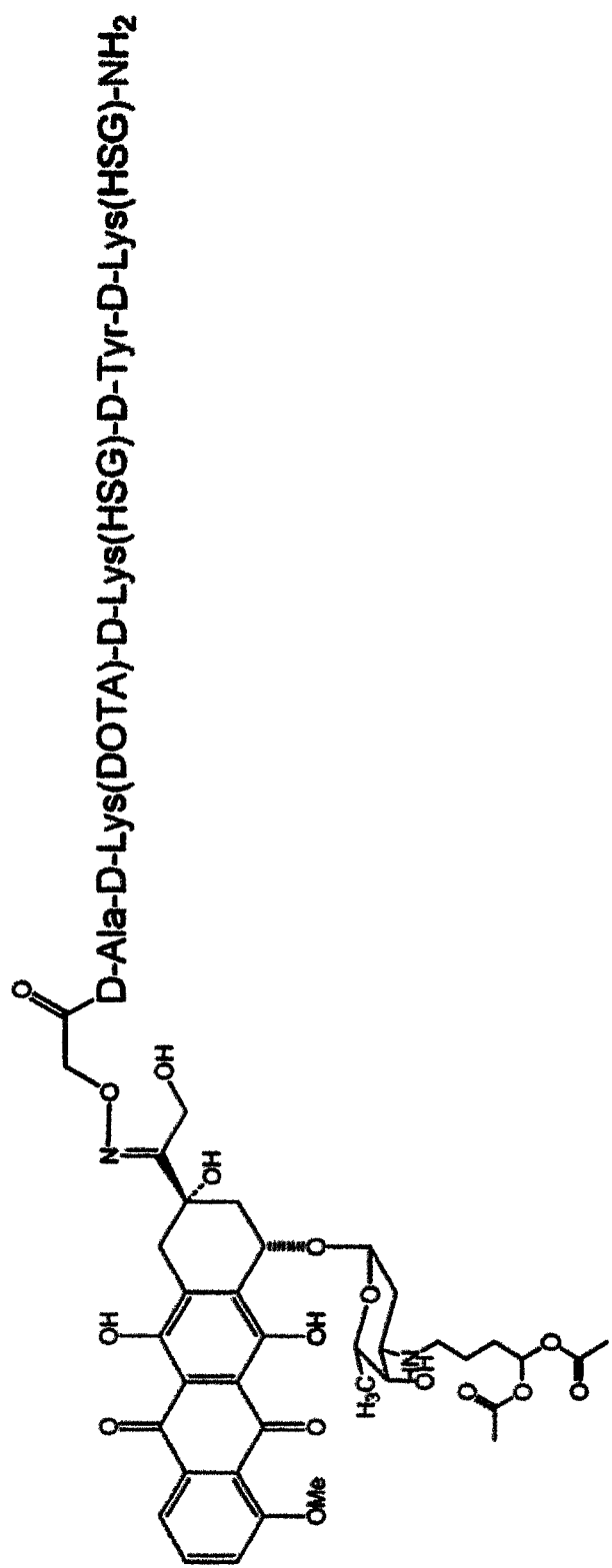
FIG. 10. Structure of IMP515.
Figure 11:
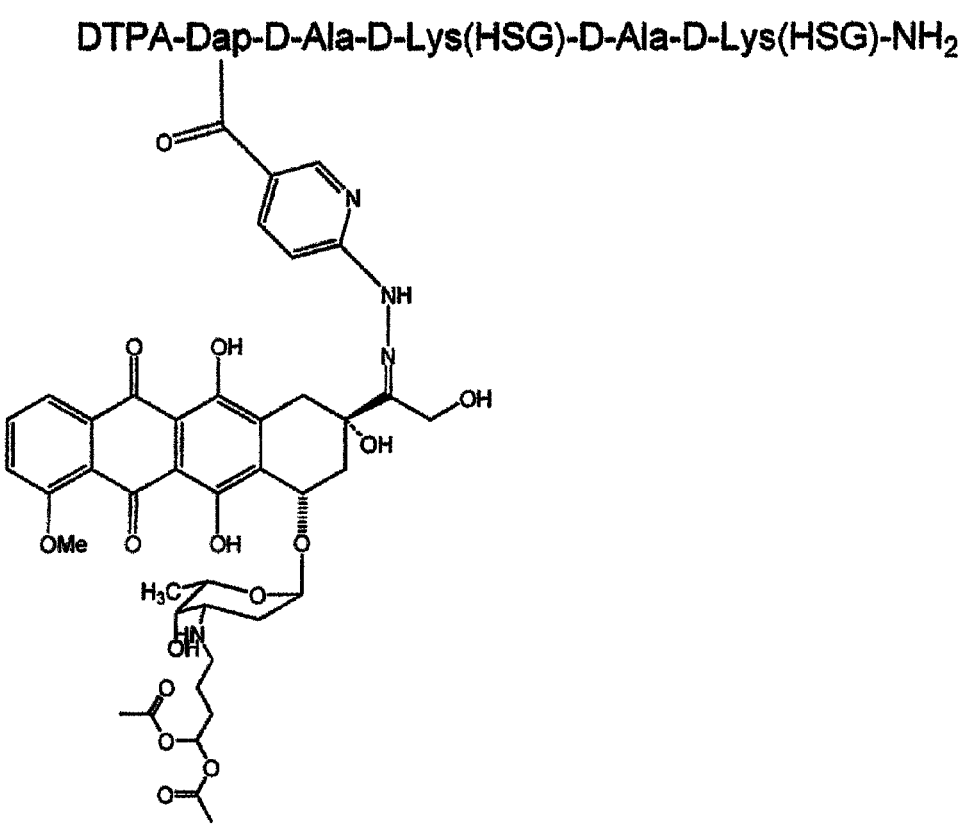
FIG. 11. Structure of IMP516.

In certain embodiments, targeting peptides (for example, targetable constructs) may be utilized to deliver P2PDox to target tissues. An exemplary peptide-conjugated P2PDox is IMP513, shown in FIG. 7. The doxorubicin-aryl hydrazone linker used to conjugate to the peptide was as disclosed in U.S. Pat. No. 7,405,320 (the Examples section of which is incorporated herein by reference). The initial P2PDox product contained a substantial amount of a cyanohydrin adduct of the ketone moiety, which was removed by dissolving the prodrug in 0.1% $NH_4OAc$ and lyophilizing the solution. After removal of the cyanohydrin group, the reaction was quantitative. An SMCC hydrazine derivatized P2PDox was also attached to peptide IMP402 (FIG. 8). Further peptide conjugates of P2PDox were produced as shown in FIG. 9 (IMP514), FIG. 10 (IMP515) and FIG. 11 (IMP516). IMP514 is an acylhydrazone-linked peptide, IMP 515 is an oxime-linked peptide and IMP516 is a pyrinehydrazone-linked peptide. The peptide-conjugated P2PDox may be delivered to target tissues using bispecific antibodies that contain binding sites for a disease-associated antigen (e.g., tumor-associated antigen) and for a hapten contained in the peptide (e.g., HSG).

Example 8

Cross-Linker Design

Figure 12:
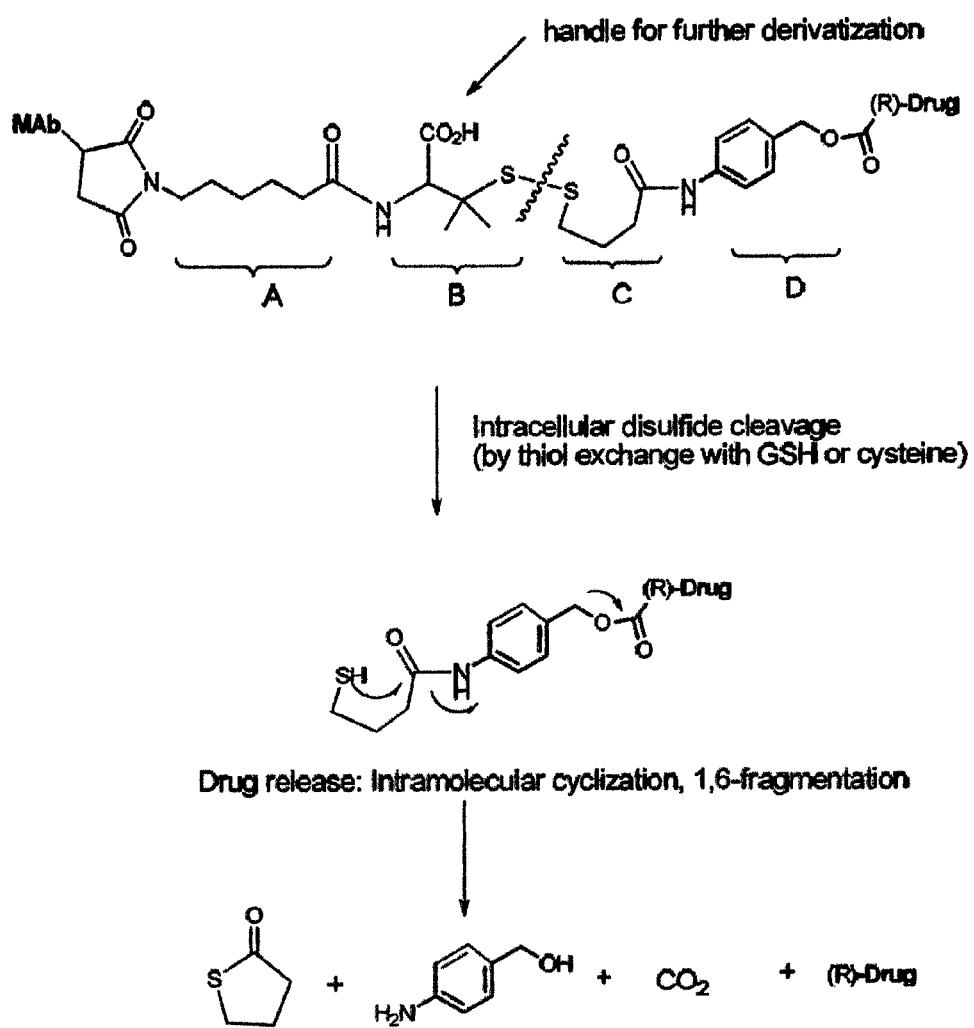
FIG. 12. Scheme for synthesis of novel cross-linkers involving a hindered disulfide system.

A new cross-linker of use in ADC formation involves a hindered disulfide system (FIG. 12). The linker is assembled from (A) maleimido acid derivative, (B) penicillamine, (C) 4-mercaptobutanoic acid, and (D) p-aminobenzyl alcohol (PABOH). The drug is attached at the PABOH end, and the antibody is attached at the maleimide (or other relevant conjugation moiety). The 'R' part of drug may be a part of the drug structure itself, and may represent 'O' (if the drug is SN-38), amino group (if the drug is doxorubicin, Pro2PDox, or any other amine containing drug), or $NH_2NH$-residue attached to COOH in the form of hydrazide, with COOH being the part structure of the drug.

The 'COOH' group on the penicillamine provides a handle for adding suitable solubilizing groups. Alternatively, the 'COOH' of penicillamine can be used for protein conjugation (active ester or derivatized to a maleimide), while the amine group is left as is or further derivatized.

The hindered disulfide ensures systemic stability of the linker, while the high concentration of intracellular thiols (e.g., cysteine, reduced GSH) cleaves the disulfide by thiol exchange. This sets up a 'domino' cleavage by intramolecular cyclization to a 5-membered lactone (favored in iew of the 5-membered geometry), with facile 1,6-fragmentation liberating PABOH, $CO_2$, and the drug. The linker thus promotes stability of ADC in the blood, while facilitating intracellular drug release.

Example 9

Additional Studies with P2PDox Conjugates

No significant difference in binding of the antibody moiety to NCI-N87 gastric carcinoma cells was observed between unconjugated hRS7 and P2PDox-hRS7 conjugated to 6 molecules of P2PDox per antibody (not shown). The lack of effect of conjugation on antibody binding to target antigen was confirmed for P2PDox-hMN-15 (anti-CEACAM6), P2PDox-hLL2 (anti-CD22) and P2PDox-hMN-24 (anti-CEACAM5) conjugates. It is concluded that conjugation of P2PDox to antibodies does not affect antibody-antigen binding activity.

The cytotoxicity of P2PDox-mAb conjugates to target cells was examined. hRS7-P2PDox and hMN-15-P2PDox were cytotoxic to MDA-MB-468, AG S, NCI-N87 and Capan-1 solid tumor cell lines (not shown). hMN-14-P2PDox was cytotoxic to Capan-1, BxPC-3 and AsPC-1 human pancreatic tumor lines and AGS, NCI-N87 and LS147T human gastric and colonic tumor lines (not shown). hLL2-P2PDOx was cytotoxic to Daudi, Raji, Ramos and NM-3 hematopoietic tumor lines (not shown). $IC_{50}$ values for the conjugates were in the nanomolar concentration range (not shown).

Figure 13:
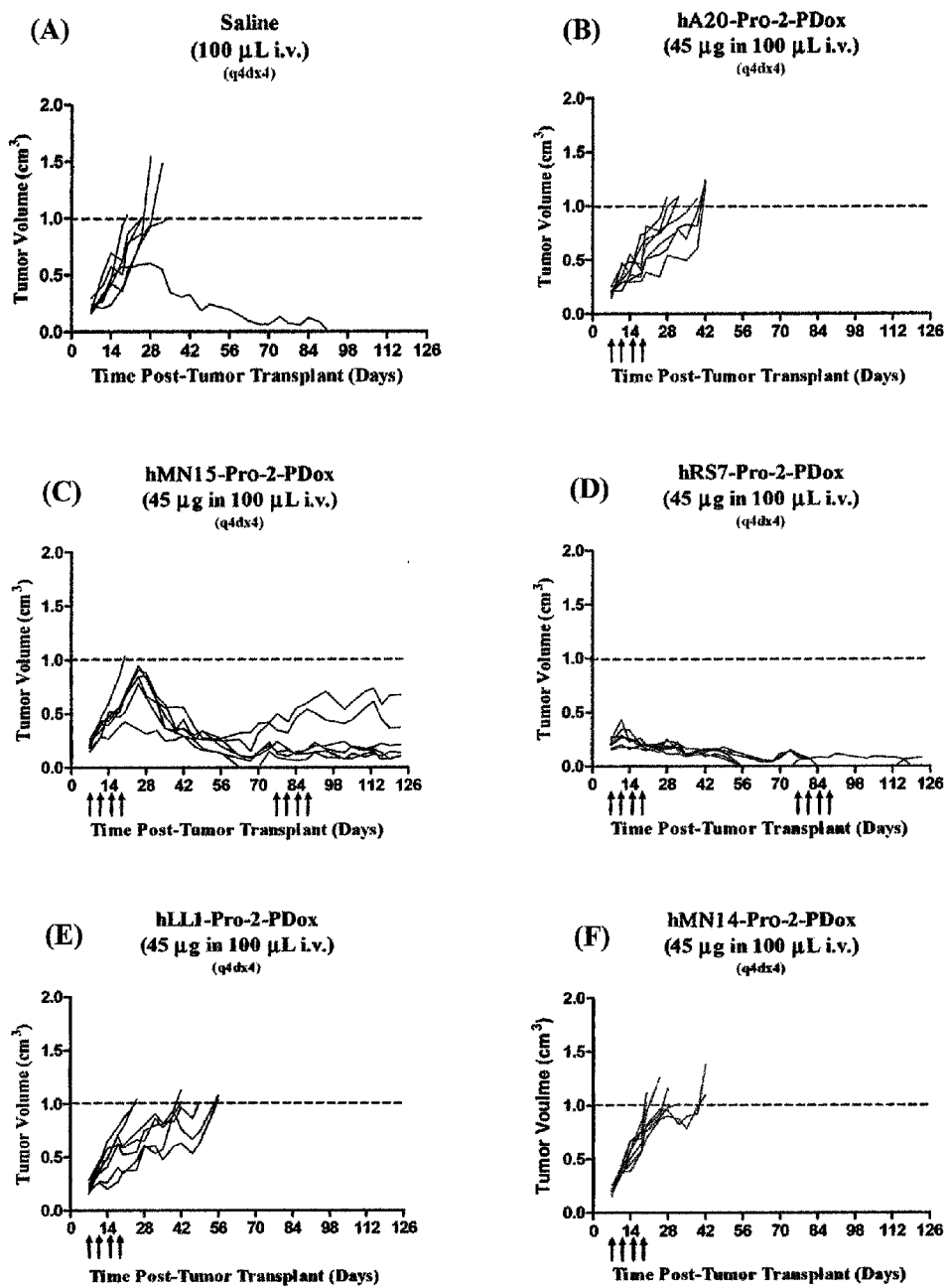
FIG. 13A. In vivo efficacy of P2PDox conjugates in nude mice with NCI-N87 human gastric cancer xenografts. Mice were administered a saline control.
FIG. 13B. In vivo efficacy of P2PDox conjugates in nude mice with NCI-N87 human gastric cancer xenografts. Mice were administered 45 µg of hA20-P2PDox as indicated by arrows.
FIG. 13C. In vivo efficacy of P2PDox conjugates in nude mice with NCI-N87 human gastric cancer xenografts. Mice were administered 45 µg of hMN-15-P2PDox as indicated by arrows.
FIG. 13D. In vivo efficacy of P2PDox conjugates in nude mice with NCI-N87 human gastric cancer xenografts. Mice were administered 45 µg of hRS7-P2PDox as indicated by arrows.
FIG. 13E. In vivo efficacy of P2PDox conjugates in nude mice with NCI-N87 human gastric cancer xenografts. Mice were administered 45 µg of hLL1-P2PDox as indicated by arrows.
FIG. 13F. In vivo efficacy of P2PDox conjugates in nude mice with NCI-N87 human gastric cancer xenografts. Mice were administered 45 µg of hMN-14-P2PDox as indicated by arrows.

Further in vivo efficacy studies were performed in nude mice implanted with NCI-N87 human gastric cancer xenografts (FIG. 13A-F). One treatment cycle with 4×45 µg of hRS7-P2PDox rapidly regressed all tumors (FIG. 13D). A second treatment cycle was initiated about 2 months after the end of the first cycle, resulting in complete regression of all but one of the hRS7-P2PDox treated animals. The hA20, hLL1 and hMN-14 conjugates had little effect on tumor progression (FIGS. 13A, 13B, 13E and 13F). Administration of P2PDox-hMN-15 resulted in a delayed regression of gastric cancer, which was less effective than the hRS7 conjugate.

Figure 19:
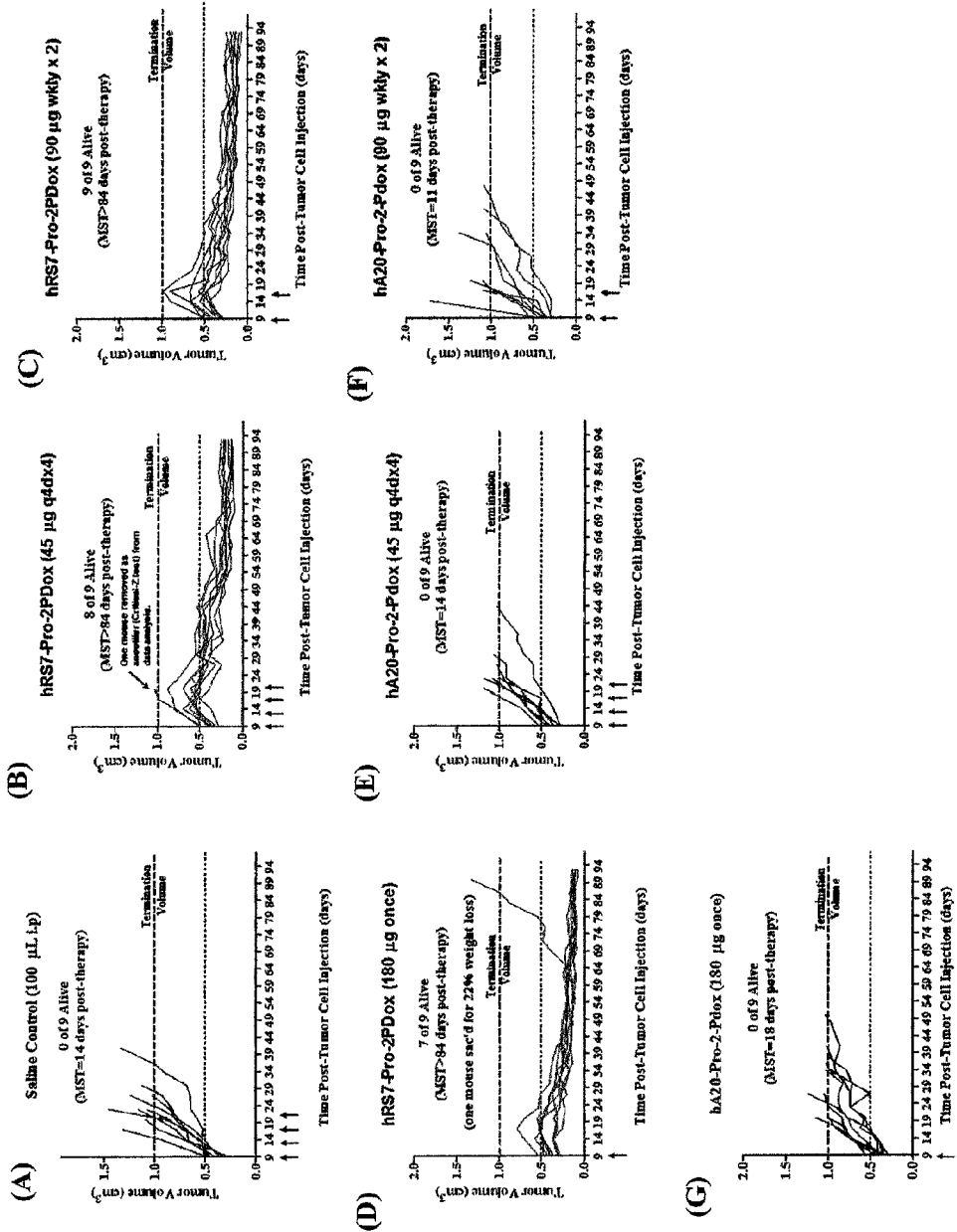
FIG. 19A. Dosing schedule study in mice injected with NCI-N87 human gastric cancer. Mice were administered a saline control.
FIG. 19B. Dosing schedule study in mice injected with NCI-N87 human gastric cancer. Mice were administered 45 µg q4dx4 of hRS7-P2PDox.
FIG. 19C. Dosing schedule study in mice injected with NCI-N87 human gastric cancer. Mice were administered 90 µg weekly×2 of hRS7-P2PDox.
FIG. 19D. Dosing schedule study in mice injected with NCI-N87 human gastric cancer. Mice were administered a single dose of 180 µg hRS7-P2PDox.
FIG. 19E. Dosing schedule study in mice injected with NCI-N87 human gastric cancer. Mice were administered 45 µg q4dx4 of hA20-P2PDox.
FIG. 19F. Dosing schedule study in mice injected with NCI-N87 human gastric cancer. Mice were administered 90 µg weekly×2 of hA20-P2PDox.
FIG. 19G. Dosing schedule study in mice injected with NCI-N87 human gastric cancer. Mice were administered a single dose of 180 µg hA20-P2PDox.

The effect of varying dosage schedule on anti-tumor efficacy was examined (FIG. 14, FIG. 19A-G). The experiment began 9 days after tumor implantation when mean tumor volume for all groups was $0.383 cm^3$, and ended on day 93 (84 days after initiation of therapy). In this study, a single dose of 180 µg, two weekly doses of 90 µg, and q4dx4 of 45 µg all resulted in significantly enhanced survival (FIG. 14, FIG. 19B-D). For the saline control, 0 of 9 mice survived (FIG. 19A). For mice receiving 45 µg q4dx4 of hRS7-P2PDox, 8 of 9 mice were alive at day 94 (FIG. 19B). For mice receiving 90 µg weekly×2 of hRS7-P2PDox, 9 of 9 mice were alive at day 94 (FIG. 19C). For mice receiving a single dose of 180 µg of hRS7-P2PDox, 78 of 9 mice were alive at day 94 (FIG. 19D).

Figure 14:
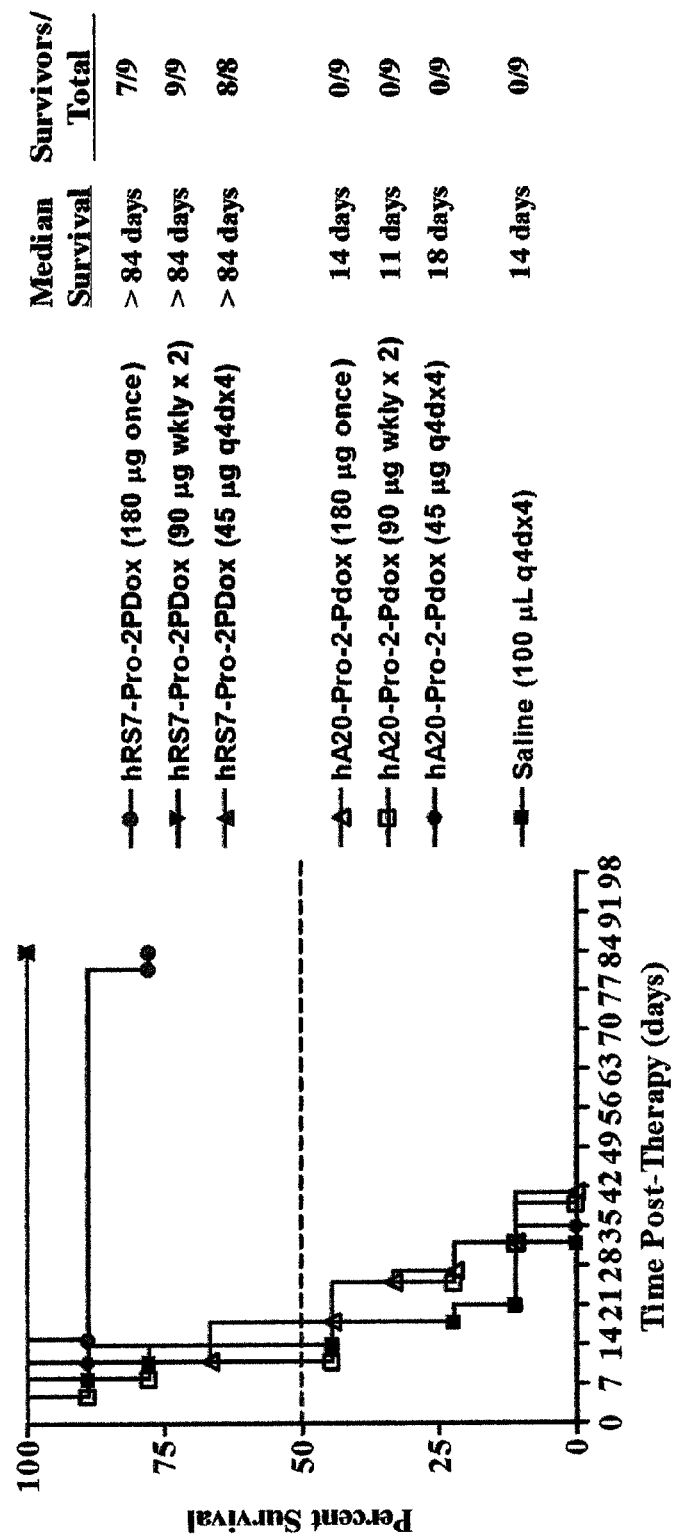
FIG. 14. Effect of different dosing schedules of hRS7-P2PDox on survival in nude mice with NCI-N87 human gastric carcinoma xenografts.

At the same dosage schedule, the control hA20 conjugate had no effect on survival (FIG. 14, FIG. 19E-F). A toxicity study showed that the three dosage schedules of hRS7-P2PDox resulted in similarly low levels of toxicity (not shown).

The hRS7-P2PDox conjugate was also effective in Capan-1 pancreatic cancer (not shown) and was more effective at inhibiting tumor growth than a hRS7-SN-38 conjugate (not shown). The hPAM4-P2PDox conjugate was also more effective at inhibiting growth of Capan-1 human pancreatic cancer than an hPAM4-SN-38 conjugate (not shown). At 63 days after Capan-1 tumor injection (with therapy starting at 1 days post-innoculation), 0 of 10 mice were alive in the saline control, 10 of 10 mice were alive in mice treated twice weekly×2 weeks with 45 µg of hPAM4-P2PDox, 2 of 10 mice were alive in mice treated twice weekly×2 weeks with 45 µg of hA20-P2PDox, 0 of 10 mice were alive in mice treated twice weekly×4 weeks with 250 µg of hPAM4-SN-38, and 0 of 10 mice were alive in mice treated twice weekly×4 weeks with 250 µg of h20-SN-38.

hRS7-P2PDox was substantially more effective than hRS7-SN-38 at inhibiting growth of PxPC-3 pancreatic cancer (not shown) and was slightly more effective than hRS7-SN-38 at inhibiting growth of MDA-MB-468 breast cancer (not shown).

Figure 15:
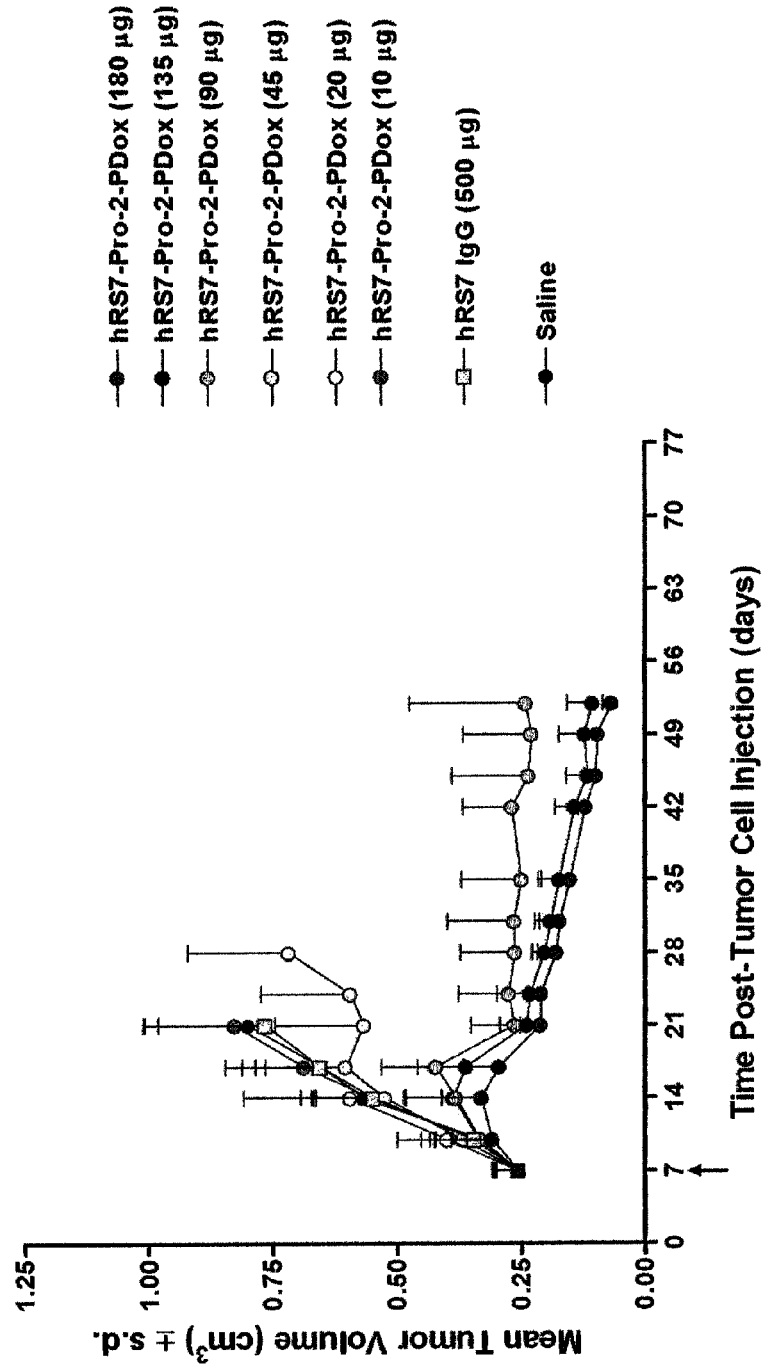
FIG. 15. Effect of different single doses of hRS7-P2PDox on growth of human gastric carcinoma xenografts.
Figure 16:
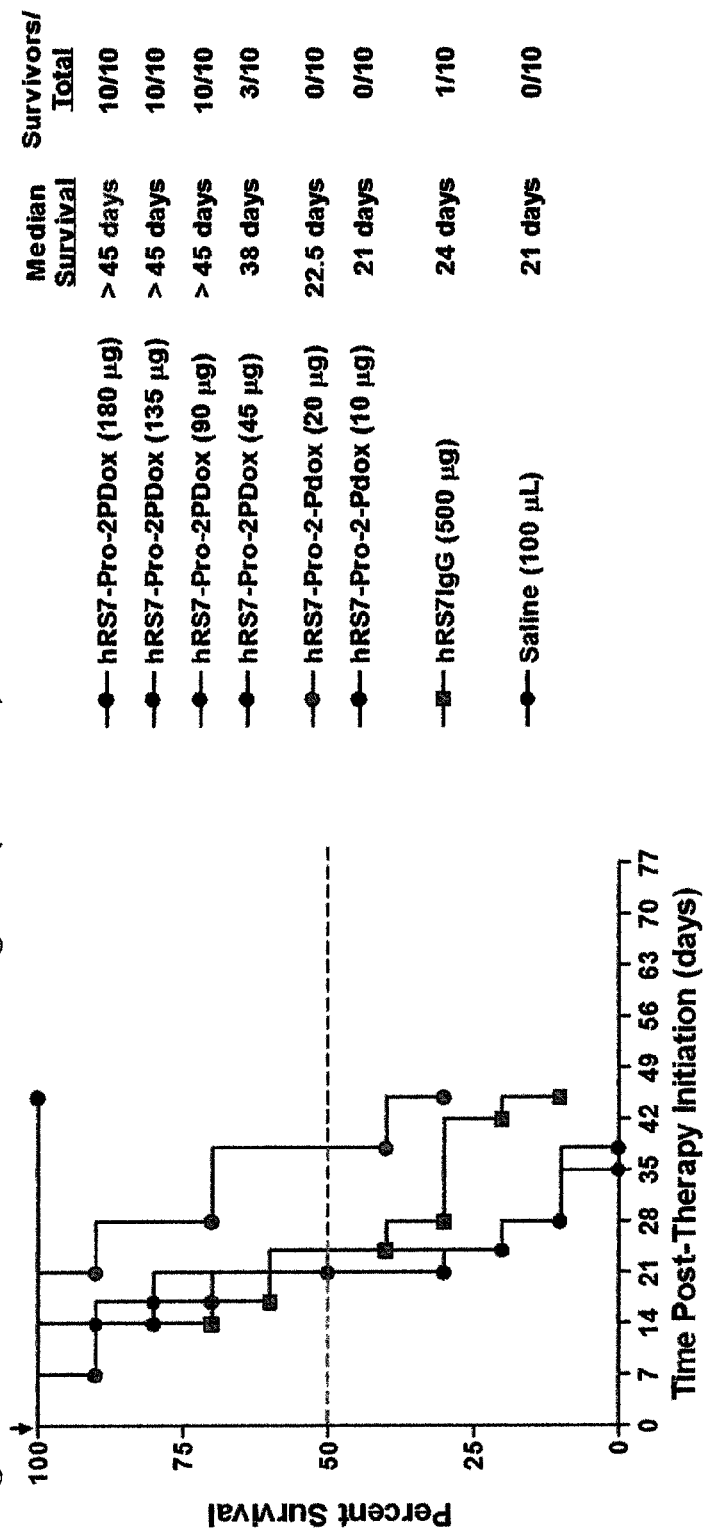
FIG. 16. Effect of different single doses of hRS7-P2PDox on survival of mice bearing human gastric carcinoma xenografts.

The effect of different single doses of hRS7-P2PDox on growth of NCI-N87 gastric carcinoma xenografts is shown in FIG. 15. Using a single dose, the maximum effect on tumor growth was observed at 90 µg or higher (FIG. 15). A single dose of 45 µg was the minimum required to see a significant survival benefit compared to saline control (FIG. 16).

Figure 17:
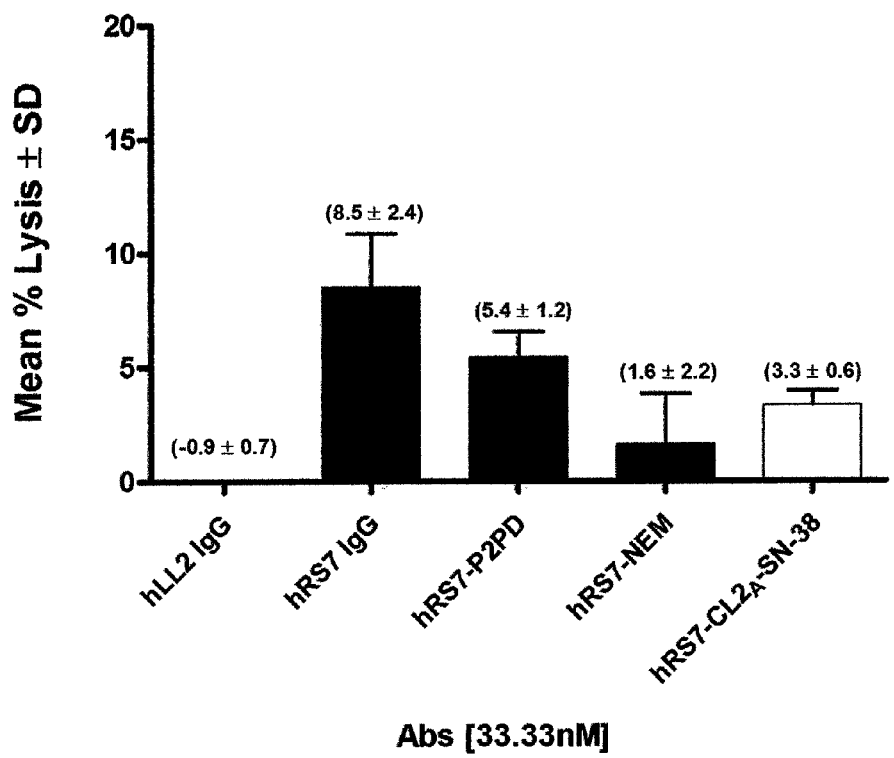
FIG. 17. ADCC of various hRS7-ADCs vs. hRS7 IgG.
Figure 18:
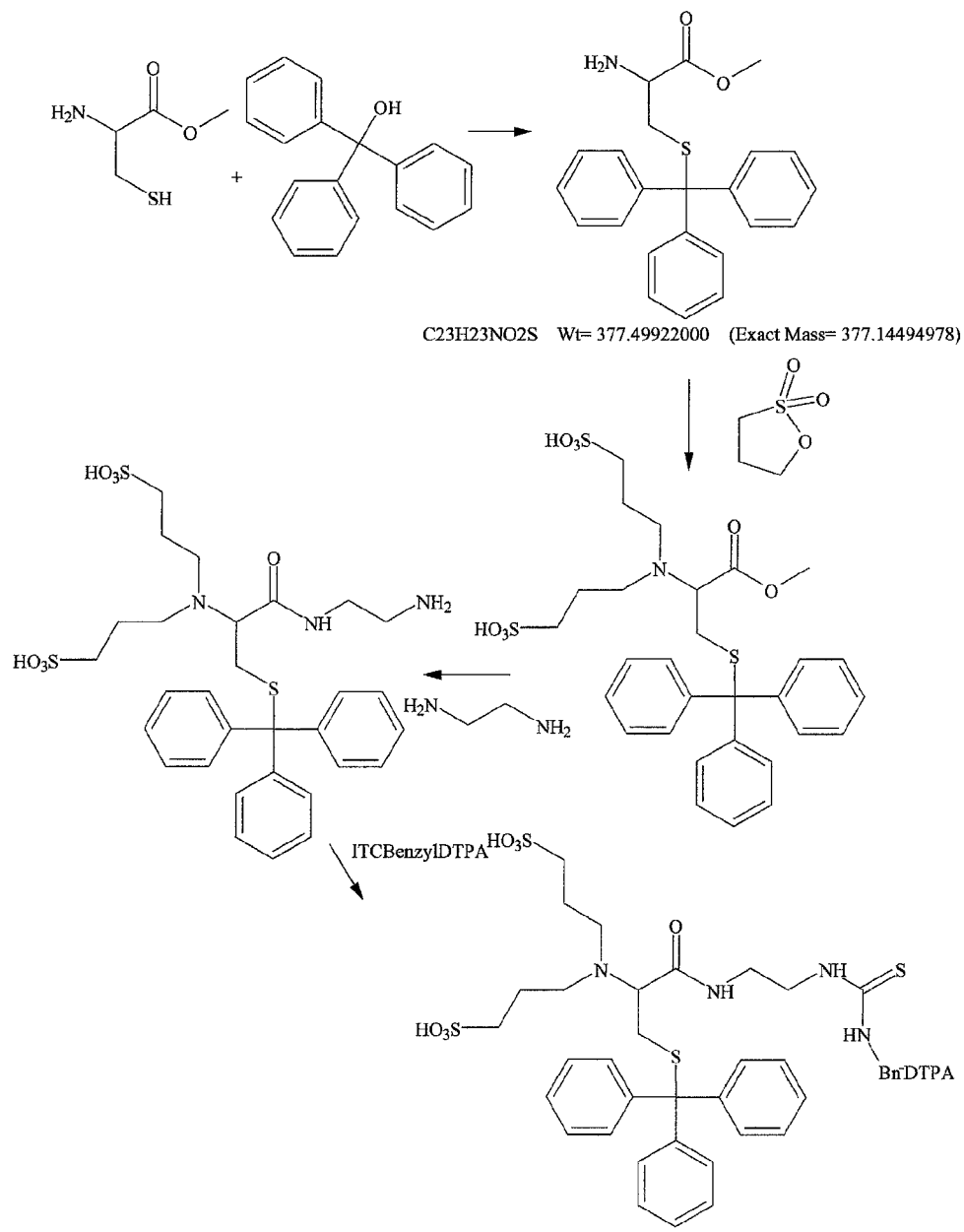
FIG. 18. Alternative scheme for producing a solubilizer for P2PDox, of use in making peptide conjugates.

The ADCC activity of various hRS7-ADC conjugates was determined in comparison to hRS7 IgG (FIG. 17). PBMCs were purified from blood purchased from the Blood Center of New Jersey. A Trop-2-positive human pancreatic adenocarcinoma cell line (BxPC-3) was used as the target cell line with an effector to target ratio of 100:1. ADCC mediated by hRS7 IgG was compared to hRS7-Pro-2-PDox, hRS7-CL2A-SN-38, and the reduced and capped hRS7-NEM. All were used at 33.3 nM.

Results are shown in FIG. 17. Overall activity was low, but significant. There was 8.5% specific lysis for the hRS7 IgG which was not significantly different from hRS7-Pro-2-PDox. Both were significantly better than hLL2 control and hRS7-NEM and hRS7-SN-38 (P<0.02, two-tailed t-test). There was no difference between hRS7-NEM and hRS7-SN-38.

Example 10

Treatment of Non-Hodgkin's Lymphoma (NHL) with P2PDox-Epratuzumab ADC

A P2PDox-epratuzumab ADC is prepared as described in Examples 1 and 3 above. Seventeen patients with previously untreated or relapsed NHL receive 4 doses of 70, 100 or 150 mg P2PDox-epratuzumab injected i.v. every two weeks. Responses are assessed by CT scans, with other evaluations including adverse event, B-cell blood levels, serum epratuzumab levels and human anti-epratuzumab (HAHA) titers.

Only occasional, mild to moderate transient injection reactions are seen and no other safety issues except neutropenia up to Grade 3 (but reversible after interrupting therapy until reduced to Grade 1) are observed. Transient B-cell depletion (up to about 25%) is observed at all dosage levels of P2PDox-epratuzumab. The objective response rate (partial responses plus complete responses plus complete responses unconfirmed) is 47% (8/17) with a complete response/complete response unconfirmed rate of 24% (4/17). Four of the eight objective responses continue for 30 weeks or more. Objective responses are observed at all dose levels of P2PDox-epratuzumab. All serum samples evaluated for human anti-epratuzumab antibody (HAHA) are negative.

Example 11

Treatment of Chronic Lymphocytic Leukemia (CLL) with P2PDox-Veltuzumab ADC

Patients with previously untreated or relapsed CLL receive 4 doses of 70, 100 or 150 mg P2PDox-veltuzumab injected i.v. every two weeks. Only occasional mild to moderate transient injection reactions are seen and no other safety issues are observed, except for neutropenia, which can be controlled by interrupting therapy until improved or administering a G-CSF leukocyte stimulator, as per conventional practice. Rapid B-cell and CLL ablation is observed at all dosage levels of P2PDox-veltuzumab, but more strikingly at the two highest doses given for at least 4 weeks. Objective responses are observed at all dose levels of P2PDox-veltuzumab, but with particularly high responses of 30% (mostly partial responses) at the highest dose. All serum samples evaluated for human anti-veltuzumab antibody (HAHA) are negative.

Example 12

Treatment of Triple Negative Breast Cancer with P2PDox-hRS7 ADC

P2PDox-hRS7 ADC is prepared as described in Examples 1 and 3 above. Patients with triple-negative breast cancer who had failed at least two standard therapies receive 3 cycles of 70 mg P2PDox-hRS7 injected i.v. every 3 weeks. Objective responses are observed at this dose level of P2PDox-hRS7, with an average decrease in tumor volume of 35%, after two cycles of therapy. All serum samples evaluated for human anti-hRS7 antibody (HAHA) are negative.

Example 13

Treatment of Metastatic Colon Cancer with P2PDox-hMN-15 ADC

A 52-year old man with metastatic colon cancer (3-5 cm diameters) to his left and right liver lobes, as well as a 5 cm metastasis to his right lung, and an elevated blood CEA value of 130 ng/mL, is treated with a 150 mg dose of hMN-15 anti-TROP-2 conjugated with P2PDox at 4 drug molecules per IgG, administered by slow intravenous infusion every other week for 4 doses. Upon CT evaluation 8 weeks from treatment begin, a 25% reduction of the total mean diameters of the 3 target lesions is measured, thus constituting a good stable disease response by RECIST1.1 criteria. At the same time, his blood CEA titer is reduced to 30 ng/mL. Repeated courses of therapy continue as his neutropenia normalizes.

A 62-year old man with metastatic ductal adenocarcinoma of the pancreas, who has relapsed after prior therapies with FOLFIRINOX followed by Nab-taxol (Abraxane®) plus gemcitabine is given PAM4-P2PDox ADC at a dose of 120 mg every other week for 4 courses, and after a 3-week delay, another course of 2 injections 2 weeks apart are given intravenously. The patient shows some nausea and transient diarrhea with the therapy, and also Grade 3 neutropenia after the first course, which recovers before the second course of therapy. CT measurements made at 8 weeks following start of therapy show an 18% shrinkage of the sum of the 3 target lesions in the liver, as compared to the pretreatment baseline measurements, constituting stable disease by RECIST 1.1 criteria. Also, the patient's CA19-9 blood titer is reduced by 55% from a baseline value of 12,400. His general symptoms of weakness, fatigue and abdominal discomfort also improve considerably, including regaining his appetite and a weight increase of 2 kg during the following 6 weeks.

Example 14

Therapy of Systemic Lupus Erythematosus (SLE) with Epratuzumab-P2PDox

An open-label, single-center study of patients with moderately active SLE (total British Isles Lupus Assessment Group (BILAG) score 6 to 12) is conducted. Patients receive dosages of epratuzumab-P2PDox (conjugated at a drug/antibody ratio of 3.5) of 10, 20, 40 and 60 mg conjugate i.v. every other week for 3 injections, repeated 4 months later. Evaluations include safety, SLE activity (BILAG), blood levels of B and T cells, and human anti-epratuzumab antibody (HAHA) titers.

Total BILAG scores decrease by at least 50% in all patients, with 92% having decreases continuing to at least 18 weeks. Almost all patients (93%) experience improvement in at least one BILAG B- or C-level disease activity at 6, 10 and 18 weeks. Additionally, 3 patients with multiple BILAG B involvement at baseline have completely resolved all B-level disease activities by 18 weeks. Epratuzumab-P2PDox is well tolerated, with no evidence of immunogenicity or significant changes in T cells, immunoglobulins or autoantibody levels. B-cell levels decrease by an average of 35% at 18 weeks and remain depressed for 6 months post-treatment.

Example 15

Treatment of Human Immunodeficiency Virus Infection with P4/D10-P2PDox

To demonstrate the efficacy of an immunoconjugate against HIV-1, murine monoclonal antibody (Mab) against the envelope antigen of HIV (P4/D10) is conjugated with P2PDox, as described in Examples 1 and 3 above, and tested against infected cells, in vitro and in vivo. P4/D10-P2PDox is tested in vitro for its efficacy in eliminating HIV-1-infected cells among non-infected cells and in a mouse model by removing HIV-1/MuLV (murine leukemia virus) infected syngeneic cells from the intraperitoneal cavity.

Jurkat T-cells are infected with HIV-1$_{IIIB}$ by mixing 5–10× $10^6$ cells with 100×TCID$_{50}$ HIV-1$_{IIIB}$ and incubating for 1 h at 37° C. The cells are washed in medium and incubated at 37° C. Every third day, medium is changed and supernatant checked for p24 production. When close to 100% of the cells are infected, different proportions of HIV-1$_{IIIB}$-infected cells are mixed with uninfected cells. The cells are treated with serial dilutions of antibodies or serum from 100 to 0.00001 µg/ml. After seven days of culture at 37° C., HIV-1 p24 inhibition is measured.

A human T-cell line, CEM-1B, with a genetically integrated MuLV genome is infected with HIV-1$_{IIIB}$, which leads to the production of pseudoviruses with the HIV-1 genome and the MuLV envelope (Adang et al., PNAS USA 1999, 96:12749-753; Hinkula et al., Cells Tissues Organs 2004, 177:169-184). These virus supernatants are used to infect splenocytes from C57B1/6xDBA F1 $K^{b/d}$ mice transgenic for HLA-A201. Isogenic mice are challenged with HIV-1$_{IIIB}$/MuLV infected splenocytes i.p. and are immediately given conjugated antibodies or free antibodies i.p. Ten days after challenge, mice are sacrificed and peritoneal cells collected. Peritoneal cells are pelleted and added to $1 \times 10^6$ HIV susceptible Jurkat T-cells or human PBMC grown in 24-well plates. From these secondary cultures, supernatant is removed and fresh medium added every 3-4 days. The amount of infectious HIV recovered in the supernatant is measured for 3 weeks by p24 ELISA.

When 3% HIV-1$_{IIIB}$ infected Jurkat cells are mixed with 97% uninfected cells, P4/D10-P2PDox mediates a significantly stronger inhibition of intercellular spread of HIV-1 infection than free P4/D10 or P2PDox-conjugated control antibody, hLL1, at a concentration of 0.005 µg/ml. Similar results are seen at all other concentrations of infected and uninfected cells. No infectious virus are found in the cultures treated with P4/D10-P2PDox, since no p24 production is detected after transfer of supernatants from these cell cultures to uninfected Jurkat cells.

To test the efficacy of F'4/D10-P2PDox in vivo, mice are given isogeneic HIV/MuLV-infected cells together with conjugates intraperitoneally. Peritoneal cells are harvested 10 days later and infectious HIV is demonstrated in all controls. The P4/D10-P2PDox protects mice completely against challenge with HIV-1 infected primary lympoid cells. No infectious HIV are recovered from peritoneal cells after challenge and treatment with 5 µg of P4/D10-P2PDox. Mice treated with 100 µg of unconjugated P4/D 10 antibody are all positive for p24 production. None of the P2PDox-conjugated control antibodies (hLL1 or hRS7) provide any protection at doses of 100-200 µg.

All patents and other references cited in the specification are indicative of the level of skill of those skilled in the art to which the invention pertains, and are incorporated herein by reference, including any Tables and Figures, to the same extent as if each reference had been incorporated by reference individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

What is claimed is:

1. A conjugate comprising:
   a) pro-2-pyrrolinodoxorubicin (P2PDox), wherein P2PDox is N-(4,4-diacetoxybutyl)doxorubicin; and
   b) an antibody or antigen-binding antibody fragment attached to the P2PDox.

2. The conjugate of claim 1, wherein antibody or antigen-binding antibody fragment binds to a tumor-associated antigen.

3. The conjugate of claim 1, wherein the antibody, antigen-binding antibody fragment, targeting peptide, or non-antibody cell-targeting construct binds to an antigen selected from the group consisting of CTLA4, PD1, PD-L1, carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD47, CD52, CD54, CD55, CD59, CD64, CD66a-e, CD67, CD70, CD70L, CD74, CD79a, CD80, CD83, CD95, CD126, CD133, CD138, CD147, CD154, AFP, PSMA, CEACAM5, CEACAM-6, c-MET, B7, ED-B of fibronectin, Factor H, FHL-1, Flt-3, folate receptor, GRO-β, histone H2B, histone H3, histone H4, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, IP-10, LIV-1, MAGE, mCRP, MCP-1, MIP-1A, MIP-1B, MIF, MUC1, MUC2, MUC3, MUC4, MUC5, MUC5ac, MUC16, PAM4 antigen, NCA-95, NCA-90, Ia, HM1.24, EGP-1 (TROP-2), EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product.

4. The conjugate of claim 1, wherein the antibody is selected from the group consisting of hR1 (anti-IGF-1R), hPAM4 (anti-MUC5ac), hA20 (anti-CD20), GA101 (anti-CD20), hA19 (anti-CD19), hIMMU-31 (anti-AFP), hLL1 (anti-CD74), hLL2 (epratuzumab, anti-CD22), hRFB4 (anti-CD22), hMu-9 (anti-CSAp), hL243 (anti-HLA-DR), hL243 IgG4P (anti-HLA-DR), hMN-14 (anti-CEACAM5), hMN-15 (anti-CEACAM6), hRS7 (anti-EGP-1 or anti-TROP-2), hMN-3 (anti-CEACAM6), Ab124 (anti-CXCR4) and Ab125 (anti-CXCR4).

5. The conjugate of claim 1, wherein the antibody fragment is selected from the group consisting of F(ab')$_2$, F(ab)$_2$, Fab, Fab' and scFv fragments.

6. The conjugate of claim 1, wherein the antibody or fragment thereof comprises human constant regions selected from the group consisting of IgG1, IgG2, IgG3 and IgG4.

7. The conjugate of claim 1, wherein the antibody is a non-G1m1 (nG1m1) antibody.

8. The conjugate of claim 1, wherein the antibody has a G1m3 heavy chain allotype.

9. The conjugate of claim 1, wherein the antibody has a nG1m1,2 heavy chain null allotype.

10. The conjugate of claim 1, wherein the antibody has a Km3 light chain allotype.

11. The conjugate of claim 1, wherein the antibody comprises heavy chain constant region amino acid residues arginine-214, glutamic acid-356, methionine-358 and alanine-431.

12. The conjugate of claim 1, wherein the antibody is selected from the group consisting of a monoclonal antibody, an antigen-binding fragment of a monoclonal antibody, a bispecific antibody, a multispecific antibody, and an antibody fusion protein.

13. The conjugate of claim 1, wherein the P2PDox is attached to the antibody or antibody fragment by a cross-linker selected from the group consisting of SMCC hydrazide, aminoxy, phenylhydrazide and 4-(hydrazinosulfonyl)benzoic acid.

14. The conjugate of claim 1, wherein the P2PDox comprises a maleimide moiety and is attached to the antibody, antibody fragment or peptide by reaction of the maleimide with a cysteine residue.

15. The conjugate of claim 1, wherein the P2PDox forms intramolecular cross-links with the antibody or antigen-binding antibody fragment.

16. The conjugate of claim 15, wherein the intramolecular cross-links stabilize the conjugate in vivo and prevent release of free drug in circulation.

17. A pharmaceutical composition comprising a conjugate according to claim 1.

18. A method of treating cancer, comprising administering to a subject with cancer a conjugate comprising (i) pro-2-pyrrolinodoxorubicin (P2PDox) wherein P2PDox is N-(4,4-diacetoxybutyl)doxorubicin; and (ii) an antibody or antigen-binding antibody fragment attached to the P2PDox, wherein the an antibody or antigen-binding antibody fragment binds to a tumor-associated antigen (TAA).

19. The method of claim 18, wherein the antibody, antigen-binding antibody fragment, targeting peptide, or non-antibody cell-targeting construct binds to an antigen selected from the group consisting of CTLA4, PD1, PD-L1, carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD47, CD52, CD54, CD55, CD59, CD64, CD66a-e, CD67, CD70, CD70L, CD74, CD79a, CD80, CD83, CD95, CD126, CD133, CD138, CD147, CD154, AFP, PSMA, CEACAM5, CEACAM-6, c-MET, B7, ED-B of fibronectin, Factor H, FHL-1, Flt-3, folate receptor, GRO-β, histone H2B, histone H3, histone H4, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, IP-10, LIV-1, MAGE, mCRP, MCP-1, MIP-1A, MIP-1B, MIF, MUC1, MUC2, MUC3, MUC4, MUC5, MUC5ac, MUC16, PAM4 antigen, NCA-95, NCA-90, Ia, HM1.24, EGP-1 (TROP-2), EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product.

20. The method of claim 18, wherein the antibody is selected from the group consisting of hR1 (anti-IGF-1R), hPAM4 (anti-MUC5ac), hA20 (anti-CD20), GA101 (anti-CD20), hA19 (anti-CD19), hIMMU-31 (anti-AFP), hLL1 (anti-CD74), hLL2 (anti-CD22), hRFB4 (anti-CD22), hMu-9 (anti-CSAp), hL243 (anti-HLA-DR), hL243 IgG4P (anti-HLA-DR), hMN-14 (anti-CEACAM5), hMN-15 (anti-CEACAM6), hRS7 (anti-EGP-1), hMN-3 (anti-CEACAM6), Ab124 (anti-CXCR4) and Ab125 (anti-CXCR4).

21. The method of claim 18, wherein the antibody fragment is selected from the group consisting of F(ab')$_2$, F(ab)$_2$, Fab, Fab' and scFv fragments.

22. The method of claim 18, wherein the antibody or fragment thereof comprises human constant regions selected from the group consisting of IgG1, IgG2, IgG3 and IgG4.

23. The method of claim 18, wherein the antibody is a non-G1m1 (nG1m1) antibody.

24. The method of claim 18, wherein the antibody has a G1m3 heavy chain allotype.

25. The method of claim 18, wherein the antibody has a nG1m1,2 heavy chain null allotype.

26. The method of claim 18, wherein the antibody has a Km3 light chain allotype.

27. The method of claim 18, wherein the antibody comprises heavy chain constant region amino acid residues arginine-214, glutamic acid-356, methionine-358 and alanine-431.

28. The method of claim 18, wherein the antibody is selected from the group consisting of a monoclonal antibody, an antigen-binding fragment of a monoclonal antibody, a bispecific antibody, a multispecific antibody, and an antibody fusion protein.

29. The method of claim 18, wherein the P2PDox is attached to the antibody or antibody fragment by a cross-linker selected from the group consisting of SMCC hydrazide, maleimide-containing hydroxylamine, maleimide-containing phenylhydrazine and 4-(hydrazinosulfonyl) benzoic acid.

30. The method of claim 18, wherein the P2PDox comprises a maleimide moiety and is attached to the antibody or antibody fragment by reaction of the maleimide with a cysteine residue.

31. The method of claim 18, further comprising administering at least one therapeutic agent to said individual.

32. The method of claim 31, wherein the therapeutic agent is selected from the group consisting of a drug, a prodrug, a toxin, an enzyme, a tyrosine kinase inhibitor, a sphingosine inhibitor, an immunomodulator, a cytokine, a hormone, a second antibody, a second antibody fragment, an immunoconjugate, a radionuclide, an antisense oligonucleotide, an RNAi, an anti-angiogenic agent, a pro-apoptosis agent and a cytotoxic agent.

33. The method of claim 32, wherein the drug is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyanomorpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), trans-platinum, thalidomide, thioguanine, thiotepa, teniposide, topotecan, uracil mustard, vatalanib, vinorelbine, vinblastine, vincristine, vinca alkaloids and ZD1839.

34. The method of claim 32, wherein the toxin is attached to an antibody or antigen-binding antibody fragment and is selected from the group consisting of ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

35. The method of claim 32, wherein the radionuclide is attached to an antibody or antigen-binding antibody fragment and is selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{189m}$Os, $^{192}$Ir $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{227}$Th, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br and $^{169}$Yb.

36. The method of claim 32, wherein the immunomodulator is selected from the group consisting of a cytokine, a chemokine, a stem cell growth factor, a lymphotoxin, an hematopoietic factor, a colony stimulating factor (CSF), an interferon, erythropoietin, thrombopoietin, a tumor necrosis factor (TNF), an interleukin (IL), granulocyte-colony stimulating factor (G-CSF), granulocyte macrophage-colony stimulating factor (GM-CSF) and a stem cell growth factor designated "S1 factor".

37. The method of claim 36, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-.alpha., tumor necrosis factor-.beta., mullerian-inhibiting substance, mouse gonadotropin-associated peptide, inhibin, activin, vascular endothelial growth factor, integrin, thrombopoietin (TPO), NGF-.beta., platelet-growth factor, TGF-.alpha., TGF-.beta., insulin-like growth factor-I, insulin-like growth factor-II, erythropoietin (EPO), osteoinductive factors, interferon-.alpha., interferon-.beta., interferon-.gamma., macrophage-CSF (M-CSF), IL-1, IL-1.alpha., IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

38. The method of claim 36, wherein the chemokine is selected from the group consisting of RANTES, MCAF, MIP1-alpha, MIP1-beta and IP-10.

39. The method of claim 32 wherein the second antibody binds to an antigen selected from the group consisting of CTLA4, PD1, PD-L1, carbonic anhydrase IX, CCL19, CCL21, CSAp, CD1, CD1a, CD2, CD3, CD4, CD5, CD8, CD11A, CD14, CD15, CD16, CD18, CD19, IGF-IR, CD20, CD21, CD22, CD23, CD25, CD29, CD30, CD32b, CD33, CD37, CD38, CD40, CD40L, CD45, CD46, CD47, CD52, CD54, CD55, CD59, CD64, CD66a-e, CD67, CD70, CD70L, CD74, CD79a, CD80, CD83, CD95, CD126, CD133, CD138, CD147, CD154, AFP, PSMA, CEACAM5, CEACAM-6, c-MET, B7, ED-B of fibronectin, Factor H, FHL-1, Flt-3, folate receptor, GRO-β, histone H2B, histone H3, histone H4, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, IP-10, LIV-1, MAGE, mCRP, MCP-1, MIP-1A, MIP-1B, MIF, MUC1, MUC2, MUC3, MUC4, MUC5, MUC5ac, MUC16, PAM4 antigen, NCA-95, NCA-90, Ia, HM1.24, EGP-1 (TROP-2), EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product.

40. The method of claim 18, wherein the cancer is a solid tumor or a hematopoietic cancer.

41. The method of claim 18, wherein the cancer is selected from the group consisting of B-cell lymphoma, B-cell leukemia, Hodgkin's disease, T-cell leukemia, T-cell lymphoma, myeloma, colon cancer, stomach cancer, esophageal cancer, medullary thyroid cancer, kidney cancer, breast cancer, lung cancer, pancreatic cancer, urinary bladder cancer, ovarian cancer, uterine cancer, cervical cancer, testicular cancer, prostate cancer, liver cancer, skin cancer, bone cancer, brain cancer, rectal cancer, and melanoma.

42. The method of claim 41, wherein the B-cell leukemia or B-cell lymphoma is selected from the group consisting of indolent forms of B-cell lymphoma, aggressive forms of B-cell lymphoma, chronic lymphocytic leukemia, acute lymphocytic leukemia, hairy cell leukemia, non-Hodgkin's lymphoma, Hodgkin's lymphoma, Burkitt lymphoma, follicular lymphoma, diffuse B-cell lymphoma, mantle cell lymphoma and multiple myeloma.

43. The method of claim 18, wherein the P2PDox forms intramolecular cross-links with the antibody or antigen-binding antibody fragment.

44. The conjugate of claim 43, wherein the intramolecular cross-links stabilize the conjugate in vivo and prevent release of free drug in circulation.

45. A method of delivering 2-pyrrolinodoxorubicin to a target cell, comprising exposing the target cell to a conjugate according to claim 1, wherein the conjugate is taken up by the cell and 2-pyrrolinodoxorubicin is released from the conjugate.

* * * * *